US009090685B2

(12) United States Patent
Ledbetter et al.

(10) Patent No.: US 9,090,685 B2
(45) Date of Patent: Jul. 28, 2015

(54) ANTIBODIES TO TGF-BETA

(71) Applicants: Genzyme Corporation, Cambridge, MA (US); Optein, Inc., Wilmington, DE (US)

(72) Inventors: Steven R. Ledbetter, Westborough, MA (US); Celia Patricia Hart, Noyarey (FR); Robert G. Holgate, Royston (GB); Lutz U. Jermutus, Buckhurst Hill (GB); Catriona L. Buchanan, Sawston (GB); Alexander R. Duncan, Girton (GB); Donna K. Finch, Horseheath (GB)

(73) Assignees: Genzyme Corporation, Cambridge, MA (US); Optein, Inc., Wilmington, DE (US)

( * ) Notice: Subject to any disclaimer, the term of this patent is extended or adjusted under 35 U.S.C. 154(b) by 0 days.

(21) Appl. No.: 14/059,241

(22) Filed: Oct. 21, 2013

(65) Prior Publication Data

US 2014/0127230 A1    May 8, 2014

Related U.S. Application Data

(60) Division of application No. 13/615,388, filed on Sep. 13, 2012, now Pat. No. 8,591,901, which is a division of application No. 12/724,347, filed on Mar. 15, 2010, now Pat. No. 8,383,780, which is a continuation of application No. 11/350,906, filed on Feb. 8, 2006, now Pat. No. 7,723,486.

(60) Provisional application No. 60/651,343, filed on Feb. 8, 2005.

(51) Int. Cl.
| | |
|---|---|
| *C12N 15/13* | (2006.01) |
| *C07H 21/04* | (2006.01) |
| *C07K 16/22* | (2006.01) |
| *C12P 21/08* | (2006.01) |
| *A61K 39/00* | (2006.01) |

(52) U.S. Cl.
CPC ............ *C07K 16/22* (2013.01); *A61K 2039/505* (2013.01); *C07K 2316/96* (2013.01); *C07K 2317/21* (2013.01); *C07K 2317/565* (2013.01); *C07K 2317/622* (2013.01); *C07K 2317/73* (2013.01); *C07K 2317/74* (2013.01)

(58) Field of Classification Search
None
See application file for complete search history.

(56) References Cited

U.S. PATENT DOCUMENTS

| | | | |
|---|---|---|---|
| 5,543,143 | A | 8/1996 | Reed |
| 5,565,332 | A | 10/1996 | Hoogenboom et al. |
| 5,571,714 | A | 11/1996 | Dasch et al. |
| 5,824,655 | A | 10/1998 | Border |
| 6,407,213 | B1 | 6/2002 | Carter et al. |
| 7,723,486 | B2 | 5/2010 | Ledbetter et al. |

FOREIGN PATENT DOCUMENTS

| | | |
|---|---|---|
| EP | 0023940 A1 | 2/1981 |
| EP | 0184187 A2 | 6/1986 |
| GB | 2188638 A | 10/1987 |
| WO | WO 92/01047 | 1/1992 |
| WO | WO 93/06213 | 4/1993 |
| WO | WO 93/10423 | 5/1993 |
| WO | WO 94/13804 | 6/1994 |
| WO | WO 97/13844 | 4/1997 |
| WO | WO 97/29131 | 8/1997 |
| WO | WO 00/34784 | 6/2000 |
| WO | WO 2005/056772 | 9/2000 |
| WO | WO 01/66754 | 9/2001 |
| WO | WO 2004/098637 | 11/2004 |
| WO | WO 2005/007699 | 1/2005 |
| WO | WO 2005/010049 | 2/2005 |
| WO | WO 2005/097832 | 10/2005 |

OTHER PUBLICATIONS

Foote and Winter, "Antibody framework residues affecting the conformation of the hypervariable loops," J Mol Biol, 224:487-499 (1992).
Arteaga et al., "Anti-transforming growth factor (TGF)-β antibodies inhibit breast cancer cell tumorigenicity and increase mouse spleen natural killer cell activity," J Clin Invest, 92:2569-2576 (1993).
Barbas et al., "In vitro evolution of a neutralizing human antibody to human immunodeficiency virus type 1 to enhance affinity and broaden strain cross-reactivity," Proc. Natl. Acad. Sci., 91:3809-3813 (1994).
Beiboer et al., "Guided selection of a pan carcinoma specific antibody reveals similar binding characteristics yet structural divergence between the original murine antibody and its human equivalent," J Mol. Biol., 296:833-849 (2000).
Bird et al., "Single-chain antigen-binding proteins," Science, 242:423-426 (1988).
Bonewald, "Regulation and regulatory activities of transforming growth factor β," Critical Reviews™ in Eukaryotic Gene Expression, 9(1):33-44 (1999).
Border and Noble, "Fibrosis linked to TGF-β in yet another disease," J Clin Invest, 96:655-656 (1995).
Border et al., "Suppression of experimental glomerulonephritis by antiserum against transforming growth factor β1," Nature, 346:371-374 (1990).
Border et al., "Targetting TGF-β for treatment of disease," Nat. Med., 1(10):1000-1001 (1995).

(Continued)

Primary Examiner — David Romeo
(74) Attorney, Agent, or Firm — Ropes & Gray LLP; Z. Ying Li; Gabriele A. Amodeo

(57) ABSTRACT

The present invention relates to antibody molecules, in particular antibody molecules that bind Transforming Growth Factor beta (TGFβ), and uses thereof. More particularly, the invention relates to antibody molecules that bind and preferably neutralize TGFβ1, TGFβ2 and TGFβ3, so-called "pan-specific" antibody molecules, and uses of such antibody molecules. Preferred embodiments within the present invention are antibody molecules, whether whole antibody (e.g. IgG, such as IgG1 or IgG4) or antibody fragments (e.g. scFv, Fab, dAb).

16 Claims, 9 Drawing Sheets

(56) References Cited

OTHER PUBLICATIONS

Border et al., "TGF-β," *Scientific American—Science & Medicine*, 68-77, Jan./Feb. 1995.
Border et al., "Transforming growth factor β in tissue fibrosis," *New Eng. J. Med.*, 331(19):1286-1292 (1994).
Casset et al., "A peptide mimetic of an anti-CD4 monoclonal antibody by rational design," *Biochem Biophys Res Commun.*, 307(1):198-205 (2003).
Chen et al., "Selection and analysis of an optimized anti-VEGF antibody: crystal structure of an affinity-matured Fab in complex with antigen," *J. Mol. Biol.*, 293:865-881 (1999).
Clackson et al., "Making antibody fragments using phage display libraries," *Nature* 352:624-628 (1991).
Danielpour et al , "Immunodetection and quantitation of the two forms of transforming growth factor-beta (TGF-β1 and TGF-β2) secreted by cells in culture," *J Cell. Physiol.*, 138:79-86 (1989).
Danielpour et al., "Sandwich enzyme-linked immunosorbent assays (SELISAs) quantitate and distinguish two forms of transforming growth factor-beta (TGF-β1 and TGF-β2) in complex biological fluids," *Growth Factors*, 2:61-71 (1989).
Dasch et al., "Monoclonal antibodies recognizing transforming growth factor-β.—Bioactivity neutralization and transforming growth factor β2 affinity purification," *The Journal of Immunology*, 142(5):1536-1541 (1989).
De Pascalis et al., "Grafting of "abbreviated" complementarity-determining regions containing specificity-determining residues X essential for ligand contact to engineer a less immunogenic humanized monoclonal antibody," *J Immunol.*, 169(6):3076-3084 (2002).
Edwards et al., "The remarkable flexibility of the human antibody repertoire; isolation of over one thousand different antibodies to a single protein," BLyS, *J Mol. Biol.*, 334:103-118 (2003).
EvaluatePharma: "Cambridge Antibody Technology Group Plc Announces First Quarter Results," Press Release—Retrieved from Internet: URL:http://www.evaluatepharma.com/Universal/View.aspx?type=Story&id=62796 [retrieved on Apr. 25, 2012].
Figini et al., "Panning phage antibody libraries on cells: Isolation of human Fab fragments against ovarian carcinoma using guided selection," *Cancer Res.*, 58:991-996 (1998).
Flanders et al., "Antibodies to peptide determinants in transforming growth factor β and their applications," *Biochemistry*, 27:739-746 (1988).
Gin et al., "Effect of antibody to transforming growth factor β on bleomycin induced accumulation of lung collagen in mice," *Thorax*, 48:959-966 (1993).
Gram et al., "In vitro selection and affinity maturation of antibodies from a naive combinatorial immunoglobulin library," *Proc. Natl. Acad. Sci USA*, 89:3576-3580 (1992).
Griffith et al., "Three-dimensional structure of recombinant human osteogenic protein 1: structural paradigm for the transforming growth factor β superfamily," *Proc. Natl. Acad. Sci. USA*, 93:878-883 (1996).
Griffiths et al., "Human anti-self antibodies with high specificity from phage display libraries," *The EMBO Journal*, 12(2):725-734 (1993).
Griffiths et al., "Isolation of high affinity human antibodies directly from large synthetic repertoires," *The EMBO Journal*, 13(14):3245-3260 (1994).
Haan et al., "Technology Focus—The protein engineers," *BioCentury—The Bernstein Report on BioBusiness*, 12(5):A1-A6 (2004).
Hocevar et al., "TGF-β induces fibronectin synthesis through a c-Jun N-terminal kinase-dependent, Smad4-independent pathway,"*The EMBO Journal*, 18(5):1345-1356 (1999).
Hoefer et al., "Anti-(transforming growth factor β) antibodies with predefined specificity inhibit metastasis of highly tumorigenic human xenotransplants in nu/nu mice," *Cancer Immunol. Immunother*, 41:302-308 (1995).
Holliger et al., "Engineering bispecific antibodies," *Current Opinion in Biotechnol.*, 4:446-449 (1993).
Holliger et al., "Diabodies": Small bivalent and bispecific antibody fragments, *Proc. Natl. Acad. Sci. USA*, 90:6444-6448 (1993).
Holm et al., "Functional mapping and single chain construction of the anti-cytokeratin 8 monoclonal antibody TS1," Mol. Immunol , 44:1075-1084 (2007).
Hu et al., "Minibody: A novel engineered anti-carcinoembryonic antigen antibody fragment (single-chain Fv-$C_H3$) which exhibits rapid, high-level targeting of xenografts," *Cancer Res.*, 56:3055-3061 (1996).
Hutchings et al., "Generation of naïve human antibody libraries, in Antibody Engineering," R. Kontermann and S Dübel, Editors, Antibody Engineering, Springer Laboratory Manuals, Germany, 93-108 (2001).
Ignotz et al., "Transforming growth factor-β stimulates the expression of fibronectin and collagen and their incorporation into the extracellular matrix," *J Biol. Chem.*, 261(9):4337-4345 (1986).
Jackson, "Modulation of the activity of transforming growth factor beta," *Expert Opinion on Therapeutic Patents*, 8(11):1479-1486 (1998).
Jespers et al., "Guiding the selection of human antibodies from phage display repertoires to a single epitope of an antigen," *Bio/Technology*, 12:899-903 (1994).
Khanna et al., "Transforming growth factor (TGF)-β mimics and anti-TGF-β antibody abrogates the in vivo effects of cyclosporine," *Transplantation*, 67(6):882-889 (1999).
Klimka et al., "Human anti-CD30 recombinant antibodies by guided phage antibody selection using cell panning," *British Journal of Cancer*, 83(2):252-260 (2000).
Knappik et al., "Fully synthetic human combinatorial antibody libraries (HuCAL) based on modular consensus frameworks and CDRs randomized with trinucleotides," *J Mol. Biol.*, 296:57-86 (2000).
Koide et al., "The fibronectin type III domain as a scaffold for novel binding proteins," *J. Mol. Biol.*, 284:1141-1151 (1998).
Krebs et al., "High-throughput generation and engineering of recombinant human antibodies," *Journal of Immunological Methods*, 254:67-84 (2001).
Lamminmaki et al., "Crystal structure of a recombinant anti-estradiol Fab fragment in complex with 17beta—estradiol," *J Bioi Chem.*, 276(39):36687-36694 (2001).
Längle-Rouault et al., "Up to 100-fold increase of apparent gene expression in the presence of Epstein-Barr virus *oriP* sequences and EBNA1: Implications of the nuclear import of plasmids," *Journal of Virology*, 72(7):6181-6185 (1998).
Leask and Abraham, "TGF-β signaling and the fibrotic response," FASEB J, 18:816-827 (2004).
Lee et al., "Transforming growth factor β induces vascular endothelial growth factor elaboration from pleural mesothelial cells in vivo and in vitro," Am J Respir Crit Care Med, 165:88-94 (2002).
Lei et al., "Autocrine TGFβ supports growth and survival of human breast cancer MDA-MB-231 cells," Oncogene, 21:7514-7523 (2002).
Lin et al., "Regulation of fibronectin by thyroid hormone receptors," J Mol Endocrinol, 33:445-458 (2004).
Ling et al., "Therapeutic role of TGF-β-neutralizing antibody in mouse cyclosporin A nephropathy: Morphologic improvement associated with functional preservation," *J. Am. Soc. Nephrol.*, 14:377-388 (2003).
Liu et al., "Neutralizing TGF-β1 antibody infusion in neonatal rat delays in vivo glomerular capillary formation," Kidney Int, 56:1334-1348 (1999).
Logan et al., "Effects of transforming growth factor β on scar production in the injured central nervous system of the rat," *Eur. J. Neurosci.*, 6:355-363 (1994).
Lucas et al., "The autocrine production of transforming growth factor-$β_1$ during lymphocyte activation—A study with a monoclonal antibody-based ELISA, *The Journal of Immunology*," 145(5):1415-1422 (1990).
Lyons and Moses, "Transforming growth factors and the regulation of cell proliferation," Eur J Biochem, 187:467-473 (1990).
MacCallum et al., "Antibody-antigen interactions: contact analysis and binding site topography," *J Mol Biol.*, 262(5):732-745 (1996).

(56) References Cited

OTHER PUBLICATIONS

Mach et al., "Statistical determination of the average values of the extinction coefficients of tryptophan and tyrosine in native proteins," *Analytical Biochem.*, 200:74-80 (1992).
Marasco, "Intrabodies: Turning the humoral immune system outside in for intracellular immunization," *Gene Therapy*, 4:11-15 (1997).
Marks et al., "By-passing immunization: Building high affinity human antibodies by chain shuffling," *Bio/Technology*, 10:779-783 (1992).
McCafferty et al., "Phage antibodies: Filamentous phage displaying antibody variable domains," *Nature*, 348:552-554 (1990).
Mittl et al., "The crystal structure of TGF-β3 and comparison to TGF-β2: Implications for receptor binding," *Protein Science*, 5:1261-1271 (1996).
Miyajima et al., "Antibody to transforming growth factor-β ameliorates tubular apoptosis in unilateral ureteral obstruction," *Kidney Int.*, 58:2301-2313 (2000).
Mookerjee et al, "Immunosuppression in hamsters with progressive visceral leishmaniasis is associated with an impairment of protein kinase C activity in their lymphocytes that can be partially reversed by okadaic acid or anti-transforming growth factor β antibody," Infection and Immunity, 71:2439-2446 (2003).
Nygren et al., "Scaffolds for engineering novel binding sites in proteins," *Current Opinion in Structural Biology*, 7:463-469 (1997).
Osbourn et al., "Generation of a panel of related human scFv antibodies with high affinities for human CEA," *Immunotechnology*, 2:181-196 (1996).
Padlan et al., "Structure of an antibody-antigen complex: crystal structure of the HyHEL-1 0 Fab-Iysozyme complex," *Proc Natl Acad Sci*, 86(15):5938-5942 (1989).
Persic et al., "An integrated vector system for the eukaryotic expression of antibodies or their fragments after selection from phage display libraries," *Gene*, 187:9-18 (1997).
Peters et al., "Targeting TGF-β overexpression in renal disease: maximizing the antifibrotic action of angiotensin II blockade," Kidney Int, 54:1570-1580 (1998).
Pintavorn and Ballermann, "TGF-β and the endothelium during immune injury," Kidney Int, 51:1401-1412 (1997).
Portolano et al., "Lack of promiscuity in autoantigen-specific H and L chain combinations as revealed by human H and L chain 'roulette'". J Immunol , 150(3):880-887 (1993).
Qian et al., "Binding affinity of transforming growth factor-β for its type II receptor is determined by the C-terminal region of the molecule," *J. Biol. Chem.*, 271(48):30656-30662 (1996).
Queen et al., "A humanized antibody that binds to the interleukin 2 receptor," Proc. Natl. Acad. Sci. USA, 86:10029-10033 (1989).
Rader et al., "A phage display approach for rapid antibody humanization: Designed combinatorial V gene libraries," *Proc. Natl. Acad. Sci. USA*, 95:8910-8915 (1998).
Reiter et al., "Engineering antibody Fv fragments for cancer detection and therapy: Disulfide-stabilized Fv fragments," *Nature Biotech.*, 14:1239-1245 (1996).
Riechmann et al., "Reshaping human antibodies for therapy," Nature, 332:323-327 (1988).
Roberts et al., "Mesoderm induction in *Xenopus laevis* distinguishes between the various TGF-β isoforms," *Growth Factors*, 3:277-286 (1990).
Roberts et al., "New class of transforming growth factors potentiated by epidermal growth factor: Isolation from non-neoplastic tissues," *Proc. Natl. Acad. Sci. USA*, 78(9):5339-5343 (1981).
Schlunegger et al., "An unusual feature revealed by the crystal structure at 2.2Å resolution of human transforming growth factor-β2," *Nature*, 358:430-434 (1992).

Schneider et al., "Monocyte chemoattractant protein-1 mediates collagen deposition in experimental glomerulonephritis by transforming growth factor-β," *Kidney Int.*, 56:135-144 (1999).
Shah et al., "Neutralising antibody to TGF-β$_{1,2}$ reduces cutaneous scarring in adult rodents," *J. Cell. Sci.*, 107:1137-1157 (1994).
Sheets et al., "Efficient construction of a large nonimmune phage antibody library: the production of high-affinity human single-chain antibodies to protein antigens," *Proc. Natl. Acad. Sci. USA*, 95:6157-6162 (1998).
Shen et al., "Improved expression cloning using reporter genes and Epstein-Barr virus *ori*-containing vectors," *Gene*, 156:235-239 (1995).
Shenkar et al., "Anti-transforming growth factor-β monoclonal antibodies prevent lung injury in hemorrhaged mice," *Am. J. Respir. Cell. Mol. Biol.*, 11:351-357 (1994).
Sinha et al., "Transforming growth factor-β1 signaling contributes to development of smooth muscle cells from embryonic stem cells," Am J Physiol Cell Physiol, 287:C1560-C1568 (2004).
Stemmer, "Rapid evolution of a protein in vitro by DNA shuffling," *Nature*, 370:389-391 (1994).
Tahara et al., "Synthetic peptide-generated monoclonal antibodies to transforming growth factor-β1," *Hybridoma*, 12(4):441-453 (1993).
Tempest et al., "Human antibodies specific for human TGF-β derived from phage display libraries," *Immunotechnology*, 2:306 (1996).
Thompson et al., "A fully human antibody neutralising biologically active human TGFβ2 for use in therapy," *Journal of Immunological Methods*, 227:17-29 (1999).
Thompson et al., "Affinity maturation of a high-affinity human monoclonal antibody against the third hypervariable loop of human immunodeficiency virus: Use of phage display to improve affinity and broaden strain reactivity," *J Mol. Biol.*, 256:77-88 (1996).
Tomlinson, "V-BASE sequence directory," *MRC Centre for Protein Engineering*, Cambridge, UK, http://vbase.mrc-cpe.cam.ac.uk/ (1997).
Tonegawa, "Somatic generation of antibody diversity," *Nature*, 302:575-581 (1983).
Vajdos et al., "Comprehensive functional maps of the antigen-binding site of an anti-ErbB2 antibody obtained with shotgun scanning mutagenesis," *J Mol Biol.*, 320(2):415-428 (2002).
Vaughan et al., Human antibodies by design, *Nature Biotechnology*, 16:535-539 (1998).
Vaughan et al., "Human antibodies with sub-nanomolar affinities isolated from a large non-immunized phage display library," *Nature Biotechnology*, 14(3):309-314 (1996).
Wang et al., "Transforming growth factor-β1 stimulates vascular endothelial growth factor 164 via mitogen-activated protein kinase kinase 3-p38α and p38δ mitogen-activated protein kinase-dependent pathway in murine mesangial cells," J Biol Chem, 279:33213-33219 (2004).
Ward et al., "Binding activities of a repertoire of single immunoglobulin variable domains secreted from *Escherichia coli*," *Nature*, 341(6242):544-546 (1989).
Watzka et al., "Guided selection of antibody fragments specific for human interferon γ receptor 1 from a human VH- and VL-gene repertoire," *Immunotechnology*, 3:279-291 (1998).
Wu et al., "Humanization of a murine monoclonal antibody by simultaneous optimization of framework and CDR residues," J. Mol. Biol., 294:151-162 (1999).
Yingling et al., "Development of TGF-beta signaling inhibitors for cancer therpy," Nature Review/Drug Discovery, 3:1011-1022 (2004).
Rudikoff et al., "Single amino acid substitution altering antigen-binding specificity," Proc. Natl. Acad. Sci. USA, 79:1979-1983 (1982).

ial Applications 60/651,343 (now expired), filed Feb. 8, 2005. The entire disclosure of each of these referenced applications is incorporated by reference herein.

SEQUENCE LISTING

```
<160> NUMBER OF SEQ ID NOS: 31

<210> SEQ ID NO 1
<211> LENGTH: 360
<212> TYPE: DNA
<213> ORGANISM: Artificial sequence
<220> FEATURE:
<223> OTHER INFORMATION: Synthetic sequence: Nucleotide sequence
      encoding PET1073G12 VH

<400> SEQUENCE: 1
caggtgcagc tggtgcagtc tggggctgag gtgaagaagc ctgggtcctc ggtgaaggtc      60
tcctgcaagg cttctggata cacccttcagt agcaatgtta tcagctgggt gcgccaggcc    120
```

```
cctggacaag ggctcgagtg gatggggggg gtcatccta ttgttgatat tgcgaactac    180
gcacagagat tcaagggcag agtcacgatt accgcggacg aatccactag tacaacttac    240
atggagttga gcagcctgag gtctgaggac acggccgtgt attactgtgc gagcacactt    300
ggtctcgtcc tggatgctat ggactactgg ggtcaggta cgttggtcac cgtctcctca    360
```

<210> SEQ ID NO 2
<211> LENGTH: 120
<212> TYPE: PRT
<213> ORGANISM: Artificial sequence
<220> FEATURE:
<223> OTHER INFORMATION: Synthetic sequence: Amino acid sequence of
      PET1073G12 VH

<400> SEQUENCE: 2

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120
```

<210> SEQ ID NO 3
<211> LENGTH: 5
<212> TYPE: PRT
<213> ORGANISM: Artificial sequence
<220> FEATURE:
<223> OTHER INFORMATION: Synthetic sequence: Amino acid sequence of
      PET1073G12 HCDR1

<400> SEQUENCE: 3

```
Ser Asn Val Ile Ser
1               5
```

<210> SEQ ID NO 4
<211> LENGTH: 17
<212> TYPE: PRT
<213> ORGANISM: Artificial sequence
<220> FEATURE:
<223> OTHER INFORMATION: Synthetic sequence: Amino acid sequence of
      PET1073G12 HCDR2

<400> SEQUENCE: 4

```
Gly Val Ile Pro Ile Val Asp Ile Ala Asn Tyr Ala Gln Arg Phe Lys
1               5                   10                  15

Gly
```

<210> SEQ ID NO 5
<211> LENGTH: 11
<212> TYPE: PRT
<213> ORGANISM: Artificial sequence
<220> FEATURE:

<223> OTHER INFORMATION: Synthetic sequence: Amino acid sequence of
      PET1073G12 HCDR3

<400> SEQUENCE: 5

Thr Leu Gly Leu Val Leu Asp Ala Met Asp Tyr
1               5                   10

<210> SEQ ID NO 6
<211> LENGTH: 324
<212> TYPE: DNA
<213> ORGANISM: Artificial sequence
<220> FEATURE:
<223> OTHER INFORMATION: Synthetic sequence: Nucleotide sequence
      encoding PET1073G12 VL

<400> SEQUENCE: 6
gaaacggtac tcacgcagtc tccaggtacc ctgtctttgt ctccagggga aagagccacc      60
ctctcctgca gggccagtca gagtcttggc agcagctact tagcctggta tcagcagaaa     120
cctggtcagg ctcccaggct cctcatctat ggtgcatcca gcagggcacc tggcatccca     180
gacaggttca gtggcagtgg gtctggtacc gacttcactc tcaccatcag ccgactggag     240
cctgaagatt ttgcagttta ttactgtcag cagtatgctg actcaccgat caccttcggc     300
caagggacac gactggagat taaa                                            324

<210> SEQ ID NO 7
<211> LENGTH: 108
<212> TYPE: PRT
<213> ORGANISM: Artificial sequence
<220> FEATURE:
<223> OTHER INFORMATION: Synthetic sequence: Amino acid sequence of
      PET1073G12 VL

<400> SEQUENCE: 7

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 8
<211> LENGTH: 12
<212> TYPE: PRT
<213> ORGANISM: Artificial sequence
<220> FEATURE:
<223> OTHER INFORMATION: Synthetic sequence: Amino acid sequence of
      PET1073G12 LCDR1

<400> SEQUENCE: 8

Arg Ala Ser Gln Ser Leu Gly Ser Ser Tyr Leu Ala
1               5                   10

<210> SEQ ID NO 9

<210> SEQ ID NO 9
<211> LENGTH: 7
<212> TYPE: PRT
<213> ORGANISM: Artificial sequence
<220> FEATURE:
<223> OTHER INFORMATION: Synthetic sequence: Amino acid sequence of
      PET1073G12 LCDR2

<400> SEQUENCE: 9

Gly Ala Ser Ser Arg Ala Pro
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic sequence: Amino acid sequence of
      PET1073G12 LCDR3

<400> SEQUENCE: 10

Gln Gln Tyr Ala Asp Ser Pro Ile Thr
1               5

<210> SEQ ID NO 11
<211> LENGTH: 360
<212> TYPE: DNA
<213> ORGANISM: Artificial sequence
<220> FEATURE:
<223> OTHER INFORMATION: Synthetic sequence: Nucleotide sequence
      encoding PET1074B9 VH

<400> SEQUENCE: 11
caggtgcagc tggtgcagtc tggggctgag gtgaagaagc ctgggtcctc ggtgaaggtc      60
tcctgcaagg cttctggata caccttcagt agcaatgtta tcagctgggt gcgccaggcc     120
cctggacaag gctcgagtg gatgggggg gtcatccta ttgttgatat tgcgaactac        180
gcacagagat tcaagggcag agtcacgatt accgcggacg aatccactag tacaacttac     240
atggagttga gcagcctgag gtctgaggac acggccgtgt attactgtgc gctgccacgc     300
gctttcgtcc tggatgctat ggactactgg ggtcaggta cgttggtgac cgtctcctca      360

<210> SEQ ID NO 12
<211> LENGTH: 120
<212> TYPE: PRT
<213> ORGANISM: Artificial sequence
<220> FEATURE:
<223> OTHER INFORMATION: Synthetic sequence: Amino acid sequence of
      PET1074B9 VH

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Leu Pro Arg Ala Phe Val Leu Asp Ala Met Asp Tyr Trp Gly Gln

Gly Thr Leu Val Thr Val Ser Ser
        115                 120

<210> SEQ ID NO 13
<211> LENGTH: 5
<212> TYPE: PRT
<213> ORGANISM: Artificial sequence
<220> FEATURE:
<223> OTHER INFORMATION: Synthetic sequence: Amino acid sequence of
      PET1074B9 HCDR1

<400> SEQUENCE: 13

Ser Asn Val Ile Ser
1               5

<210> SEQ ID NO 14
<211> LENGTH: 17
<212> TYPE: PRT
<213> ORGANISM: Artificial sequence
<220> FEATURE:
<223> OTHER INFORMATION: Synthetic sequence: Amino acid sequence of
      PET1074B9 HCDR2

<400> SEQUENCE: 14

Gly Val Ile Pro Ile Val Asp Ile Ala Asn Tyr Ala Gln Arg Phe Lys
1               5                   10                  15

Gly

<210> SEQ ID NO 15
<211> LENGTH: 11
<212> TYPE: PRT
<213> ORGANISM: Artificial sequence
<220> FEATURE:
<223> OTHER INFORMATION: Synthetic sequence: Amino acid sequence of
      PET1074B9 HCDR3

<400> SEQUENCE: 15

Pro Arg Ala Phe Val Leu Asp Ala Met Asp Tyr
1               5                   10

<210> SEQ ID NO 16
<211> LENGTH: 324
<212> TYPE: DNA
<213> ORGANISM: Artificial sequence
<220> FEATURE:
<223> OTHER INFORMATION: Synthetic sequence: Nucleotide sequence
      encoding PET1074B9 VL

<400> SEQUENCE: 16
gaaacggtac tcacgcagtc tccaggtacc ctgtctttgt ctccagggga aagagccacc      60
ctctcctgca gggccagtca gagtcttggc agcagctact tagcctggta tcagcagaaa     120
cctggtcagg ctcccaggct cctcatctat ggtgcatcca gcagggcacc tggcatccca     180
gacaggttca gtggcagtgg gtctggtacc gacttcactc tcaccatcag ccgactggag     240
cctgaagatt ttgcagttta ttactgtcag cagtatgctg actcaccgat caccttcggc     300
caagggacac gactggagat taaa                                            324

<210> SEQ ID NO 17
<211> LENGTH: 108
<212> TYPE: PRT
<213> ORGANISM: Artificial sequence
<220> FEATURE:
<223> OTHER INFORMATION: Synthetic sequence: Amino acid sequence of

PET1074B9 VL

<400> SEQUENCE: 17

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 18
<211> LENGTH: 12
<212> TYPE: PRT
<213> ORGANISM: Artificial sequence
<220> FEATURE:
<223> OTHER INFORMATION: Synthetic sequence: Amino acid sequence of
      PET1074B9 LCDR1

<400> SEQUENCE: 18

Arg Ala Ser Gln Ser Leu Gly Ser Ser Tyr Leu Ala
1               5                   10

<210> SEQ ID NO 19
<211> LENGTH: 7
<212> TYPE: PRT
<213> ORGANISM: Artificial sequence
<220> FEATURE:
<223> OTHER INFORMATION: Synthetic sequence: Amino acid sequence of
      PET1074B9 LCDR2

<400> SEQUENCE: 19

Gly Ala Ser Ser Arg Ala Pro
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic sequence: Amino acid sequence of
      PET1074B9 LCDR3

<400> SEQUENCE: 20

Gln Gln Tyr Ala Asp Ser Pro Ile Thr
1               5

<210> SEQ ID NO 21
<211> LENGTH: 363
<212> TYPE: DNA
<213> ORGANISM: Artificial sequence
<220> FEATURE:
<223> OTHER INFORMATION: Synthetic sequence: Nucleotide sequence
      encoding PET1287A10 VH

<400> SEQUENCE: 21
caggtgcagc tggtgcagtc tggggctgag gtgaagaagc ctgggtcctc ggtgaaagtg     60

```
tcctgcaagg cttctggagg caccttcagc acctctttca tcaattgggt gcgacaggcc    120
cctggacaag ggcttgagtg gatgggaggg atcatcccta tctttgatat aacaaactac    180
gcacagaaat ttcagagcag agtcactatt accgcggaca atccacgag caccgcctac     240 atggagctga gcagcctgcg ctctgaggac acggctgtgt attactgcgc acgcggaaat    300
ggtaactacg ccctggatgc tatggactac tggggtcagg gtacgttggt caccgtctcc    360
tca                                                                   363
```

```
<210> SEQ ID NO 22
<211> LENGTH: 121
<212> TYPE: PRT
<213> ORGANISM: Artificial sequence
<220> FEATURE:
<223> OTHER INFORMATION: Synthetic sequence: Amino acid sequence of
      PET1287A10 VH

<400> SEQUENCE: 22
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Ser
            20                  25                  30

Phe Ile Asn Trp Val Arg Gln Ala Pro Gly Gln Gly Leu Glu Trp Met
        35                  40                  45

Gly Gly Ile Ile Pro Ile Phe Asp Ile Thr Asn Tyr Ala Gln Lys Phe
    50                  55                  60

Gln Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Gly Asn Tyr Ala Leu Asp Ala Met Asp Tyr Trp Gly
                100                 105                 110

Gln Gly Thr Leu Val Thr Val Ser Ser
        115                 120

```
<210> SEQ ID NO 23
<211> LENGTH: 5
<212> TYPE: PRT
<213> ORGANISM: Artificial sequence
<220> FEATURE:
<223> OTHER INFORMATION: Synthetic sequence: Amino acid sequence of
      PET1287A10 HCDR1

<400> SEQUENCE: 23
```

Thr Ser Phe Ile Asn
1               5

```
<210> SEQ ID NO 24
<211> LENGTH: 17
<212> TYPE: PRT
<213> ORGANISM: Artificial sequence
<220> FEATURE:
<223> OTHER INFORMATION: Synthetic sequence: Amino acid sequence of
      PET1287A10 HCDR2

<400> SEQUENCE: 24
```

Gly Ile Ile Pro Ile Phe Asp Ile Thr Asn Tyr Ala Gln Lys Phe Gln
1               5                   10                  15

Ser

```
<210> SEQ ID NO 25
<211> LENGTH: 12
<212> TYPE: PRT
<213> ORGANISM: Artificial sequence
<220> FEATURE:
<223> OTHER INFORMATION: Synthetic sequence: Amino acid sequence of
      PET1287A10 HCDR3

<400> SEQUENCE: 25

Gly Asn Gly Asn Tyr Ala Leu Asp Ala Met Asp Tyr
1               5                   10

<210> SEQ ID NO 26
<211> LENGTH: 324
<212> TYPE: DNA
<213> ORGANISM: Artificial sequence
<220> FEATURE:
<223> OTHER INFORMATION: Synthetic sequence: Nucleotide sequence
      encoding PET1287A10 VL

<400> SEQUENCE: 26
gaaattgtgc tgactcagtc tccaggcacc ctgtctttgt ctccagggga aagagccacc        60
ctctcctgca gggccagtca gagtgttagc agcagctact tgcctggta ccagcagaaa        120 cctggccagg ctcccaggct cctcatctat ggtgcatcca gcagggccac tggcatccct       180
gacagattca gtggcagcgg gtctgggaca gatttcactc tcaccatcag ccgcctggag       240
cctgaagatt tcgcagtttta ttactgtcag caatattatg atagtcccat caccttcggc     300
caagggacac gactggagat taaa                                              324

<210> SEQ ID NO 27
<211> LENGTH: 108
<212> TYPE: PRT
<213> ORGANISM: Artificial sequence
<220> FEATURE:
<223> OTHER INFORMATION: Synthetic sequence: Amino acid sequence of
      PET1287A10 VL

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Asp Ser Pro
                85                  90                  95

Ile Thr Phe Gly Gln Gly Thr Arg Leu Glu Ile Lys
            100                 105

<210> SEQ ID NO 28
<211> LENGTH: 12
<212> TYPE: PRT
<213> ORGANISM: Artificial sequence
<220> FEATURE:
<223> OTHER INFORMATION: Synthetic sequence: Amino acid sequence of
      PET1287A10 LCDR1

<400> SEQUENCE: 28
```

-continued

```
Arg Ala Ser Gln Ser Val Ser Ser Ser Tyr Phe Ala
1               5                   10

<210> SEQ ID NO 29
<211> LENGTH: 7
<212> TYPE: PRT
<213> ORGANISM: Artificial sequence
<220> FEATURE:
<223> OTHER INFORMATION: Synthetic sequence: Amino acid sequence of
      PET1287A10 LCDR2

<400> SEQUENCE: 29

Gly Ala Ser Ser Arg Ala Thr
1               5

<210> SEQ ID NO 30
<211> LENGTH: 9
<212> TYPE: PRT
<213> ORGANISM: Artificial sequence
<220> FEATURE:
<223> OTHER INFORMATION: Synthetic sequence: Amino acid sequence of
      PET1287A10 LCDR3

<400> SEQUENCE: 30

Gln Gln Tyr Tyr Asp Ser Pro Ile Thr
1               5

<210> SEQ ID NO 31
<211> LENGTH: 11
<212> TYPE: PRT
<213> ORGANISM: Artificial sequence
<220> FEATURE:
<223> OTHER INFORMATION: Synthetic sequence:  Amino acid sequence of FR4

<400> SEQUENCE: 31

Trp Gly Gln Gly Thr Leu Val Thr Val Ser Ser
1               5                   10
```

ANTIBODIES TO TGF-BETA

This application is a divisional application of U.S. application Ser. No. 13/615,388, filed Sep. 13, 2012, now U.S. Pat. No. 8,591,901, which is a divisional application of U.S. application Ser. No. 12/724,347, filed Mar. 15, 2010, now U.S. Pat. No. 8,383,780, which is a continuation application of U.S. application Ser. No. 11/350,906, filed Feb. 8, 2006, now U.S. Pat. No. 7,723,486, which claims the benefit of U.S. Provisional Applications 60/651,343 (now expired), filed Feb. 8, 2005. The entire disclosure of each of these referenced applications is incorporated by reference herein.

A Sequence Listing associated with this application is submitted electronically via EFS-Web in text format, and is hereby incorporated by reference in its entirety into the specification. The name of the text file containing the Sequence Listing is 001662-0009-106-Sequence-Listing.txt. The text file, created on Jan. 13, 2014, is 15,801 bytes in size.

TECHNICAL FIELD

The present invention relates to antibody molecules, in particular antibody molecules that bind Transforming Growth Factor beta (TGFβ), and uses thereof. More particularly, the invention relates to antibody molecules that bind and preferably neutralise TGFβ1, TGFβ2 and TGFβ3, so-called "pan-specific" antibody molecules, and uses of such antibody molecules.

BACKGROUND

TGFβ was first identified in 1981 (Roberts et al., 1981). In humans there are three isoforms: TGFβ1, TGFβ2 and TGFβ3 (Swiss Prot accession numbers P01137, P08112 and P10600 respectively) which, in their biologically active state, are 25 kDa homodimers comprising two 112 amino acid monomers joined by an inter-chain disulfide bridge. TGFβ1 differs from TGFβ2 by 27, and from TGFβ3 by 22, mainly conservative amino acid changes. These differences have been mapped on the 3D structure of TGFβ determined by X-ray crystallography (Schlunegger et al., 1992; Peer et al., 1996) and the receptor binding regions have been defined (Griffith et al., 1996; Qian et al., 1996).

Human TGFβs are very similar to mouse TGFβs: human TGFβ1 has only one amino acid difference from mouse TGFβ1, human TGFβ2 has only three amino acid differences from mouse TGFβ2 and human TGFβ3 is identical to mouse TGFβ3. As a result, production of antibodies to human TGFβs in mice, including transgenic mice, may be difficult.

TGFβs are multifunctional cytokines that are involved in cell proliferation and differentiation, in embryonic development, extracellular matrix formation, bone development, wound healing, haematopoiesis, and immune and inflammatory responses (Border et al., 1995a). The deregulation of TGFβs leads to pathological processes that, in humans, have been implicated in numerous conditions, for example, birth defects, cancer, chronic inflammatory, autoimmune and fibrotic diseases (Border et al., 1994; Border et al., 1995b).

Studies have been performed in many fibrotic animal models (Border et al., 1995b; Border et al., 1994), using neutralising antibodies as antagonists, for example, glomerulonephritis (Border et al., 1990), neural scarring (Logan et al., 1994), dermal scarring (Shah et al., 1994) and lung fibrosis (Giri et al., 1993). All of the diseases represented by these models represent an unmet need for new therapeutic products (Bonewald, 1999; Jackson, 1998). However, the antibodies used in these and other animal studies have been raised in animals and their therapeutic benefit in humans may be limited because of their potential to induce immunogenic responses and their rapid pharmacokinetic clearance (Vaughan et al., 1998). Human antibodies are more desirable for treatment of TGFβ—

A variety of antibody fragments are known to be able to bind a target protein specifically and with good affinity. For example, antibody fragments comprising only the heavy chain variable (VH) and light chain variable (VL) domains joined together by a short peptide linker, known as single chain Fv (scFv), have been used extensively. Human antibodies neutralising TGFβ1 (CAT-192) or TGFβ2 (CAT-152 or Trabio™) have previously been generated (EP 0 945 464, EP 0 853 661, Thompson et al. 1999). However, the majority of TGFβ antibodies available in the art are non-human. Moreover, prior to this invention the only pan-specific monoclonal antibodies against TGFβ were rodent.

Polyclonal antibodies binding to human TGFβ1 and human TGFβ2 against both neutralising and non-neutralising epitopes have been raised in rabbit (Danielpour et al., 1989b; Roberts et al., 1990), chicken (R&D Systems, Minneapolis) and turkey (Danielpour et al., 1989c). Peptides representing partial TGFβ sequences have been also used as immunogens to raise neutralising polyclonal antisera in rabbits (Border et al., 1990; Flanders et al., 1988). Such non-human, polyclonal antibodies are unsuitable for human therapeutic use.

1D11.16 is a murine pan-specific anti-TGFβ antibody that neutralises human and mouse TGFβ1, TGFβ2 and TGFβ3 in a wide range of in vitro assays (Dasch et al., 1989; Dasch et al., 1996; R&D System product sheet for MAB1835) and is efficacious in proof-of principle studies in animal models of fibrosis (Ling et al., 2003; Miyajima et al., 2000; Schneider et al., 1999; Khanna et al., 1999; Shenkar et al., 1994). However, since 1D11.16 is a murine monoclonal antibody (Dasch et al., 1989; Dasch et al., 1996), it is unsuitable for therapeutic use in humans.

SUMMARY OF THE INVENTION

Figure 1A:
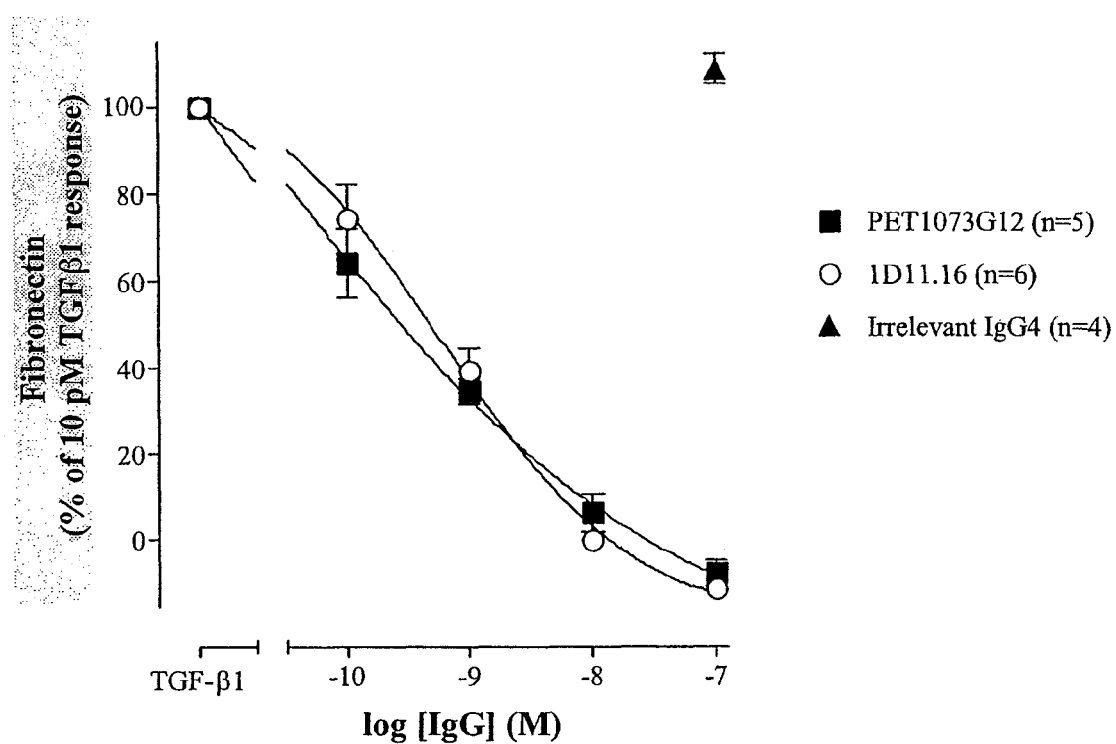
FIG. 1 shows the neutralisation (% inhibition) of TGFβ1 (a), TGFβ2 (b), or TGFβ3 (c) (10 pM)-induced fibronectin production from NHLF cells by PET1073G12 germline IgG4 (closed squares) and 1D11.16 (open circles). The closed triangle represents an irrelevant IgG4 tested at the highest concentration (100 nM). Data are shown as means±SEmean of n experiments performed in duplicate. For $IC_{50}$ values see Table 2.
Figure 1B:
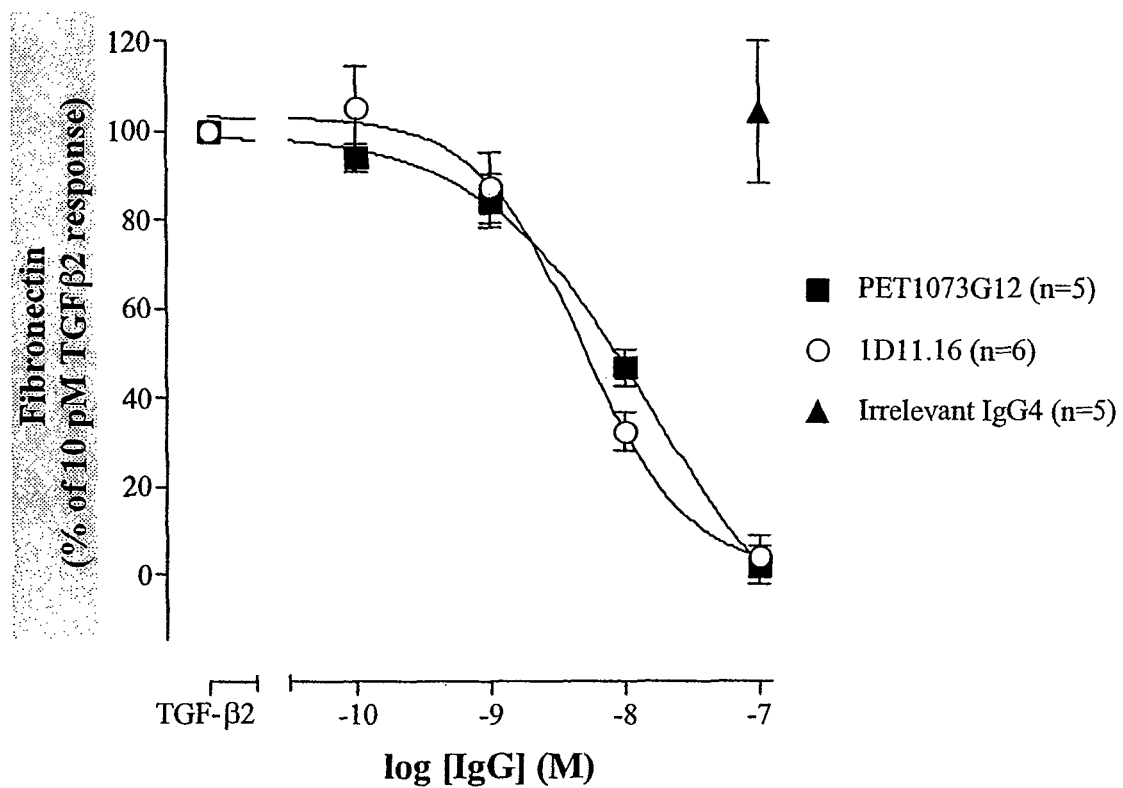
Figure 1C:
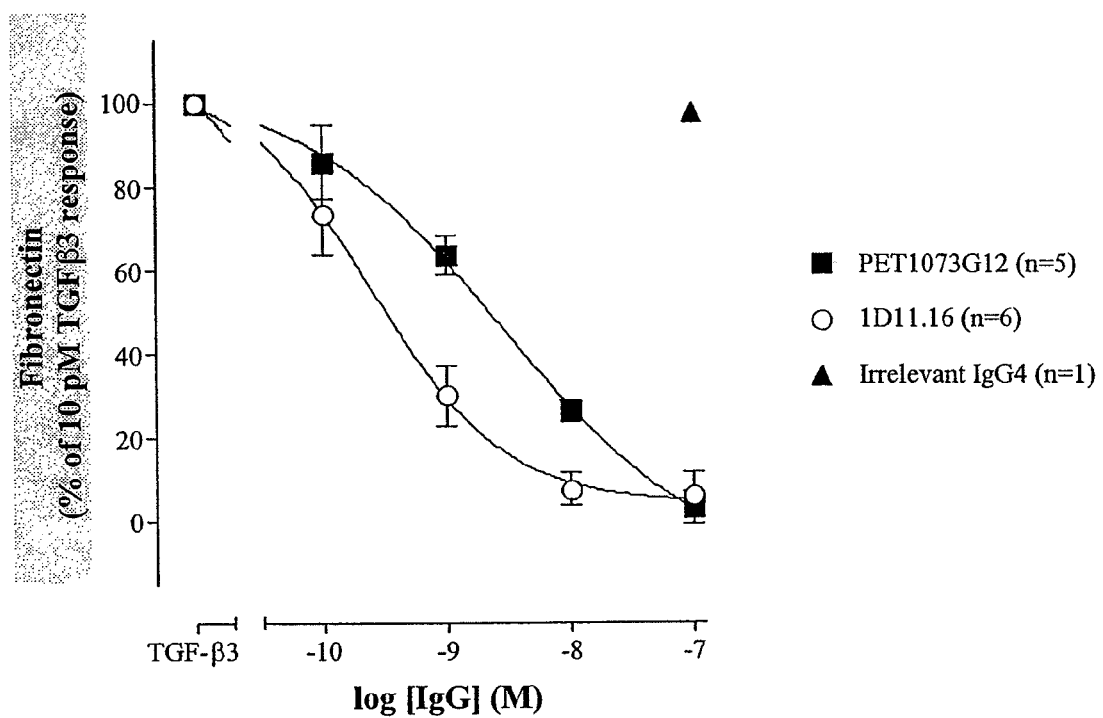
Figure 2A:
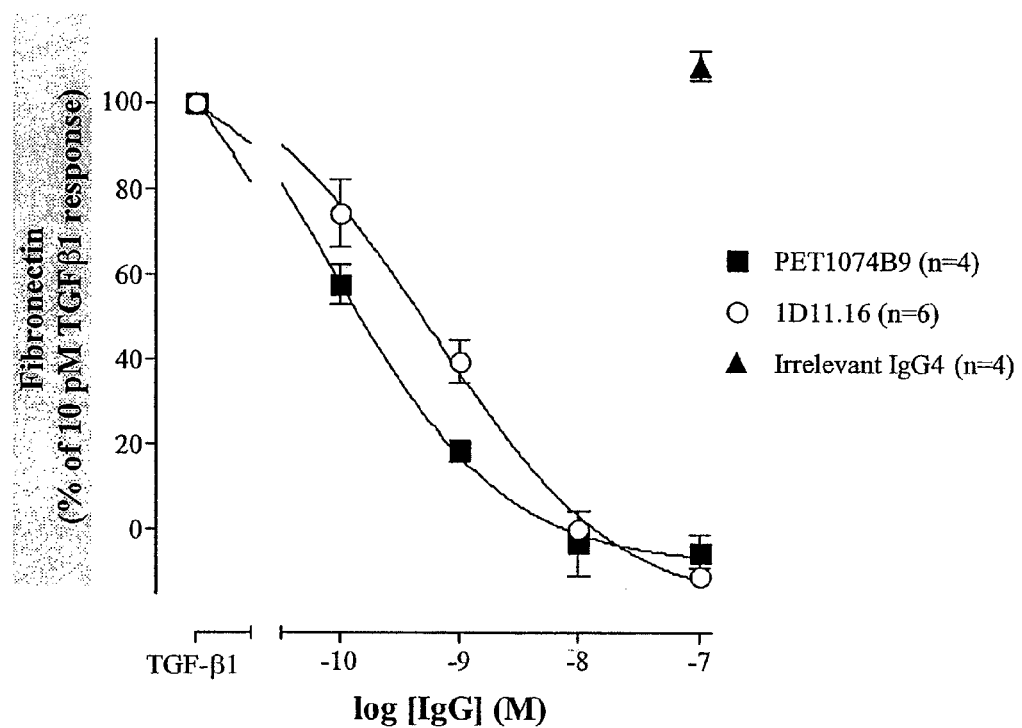
FIG. 2 shows the neutralisation (% inhibition) of TGFβ1 (a), TGFβ2 (b), or TGFβ3 (c) (10 pM)-induced fibronectin production from NHLF cells by PET1074B9 germline IgG4 (closed squares) and 1D11.16 (open circles). The closed triangle represents an irrelevant IgG4 tested at the highest concentration (100 nM). Data are shown as means±SEmean of n experiments performed in duplicates. For $IC_{50}$ values see Table 2.
Figure 2B:
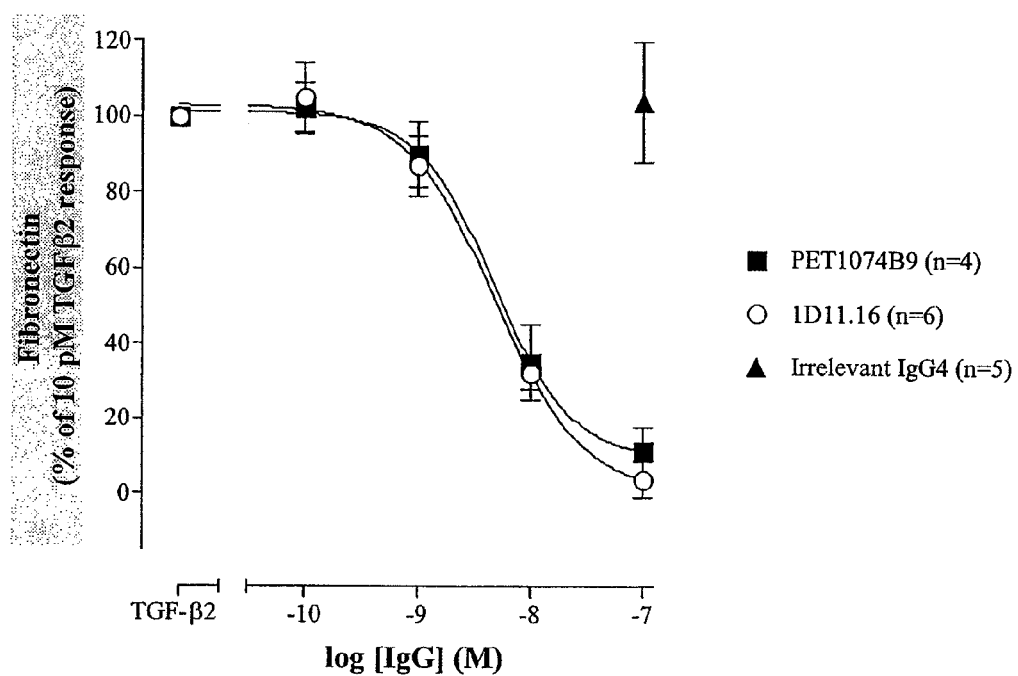
Figure 2C:
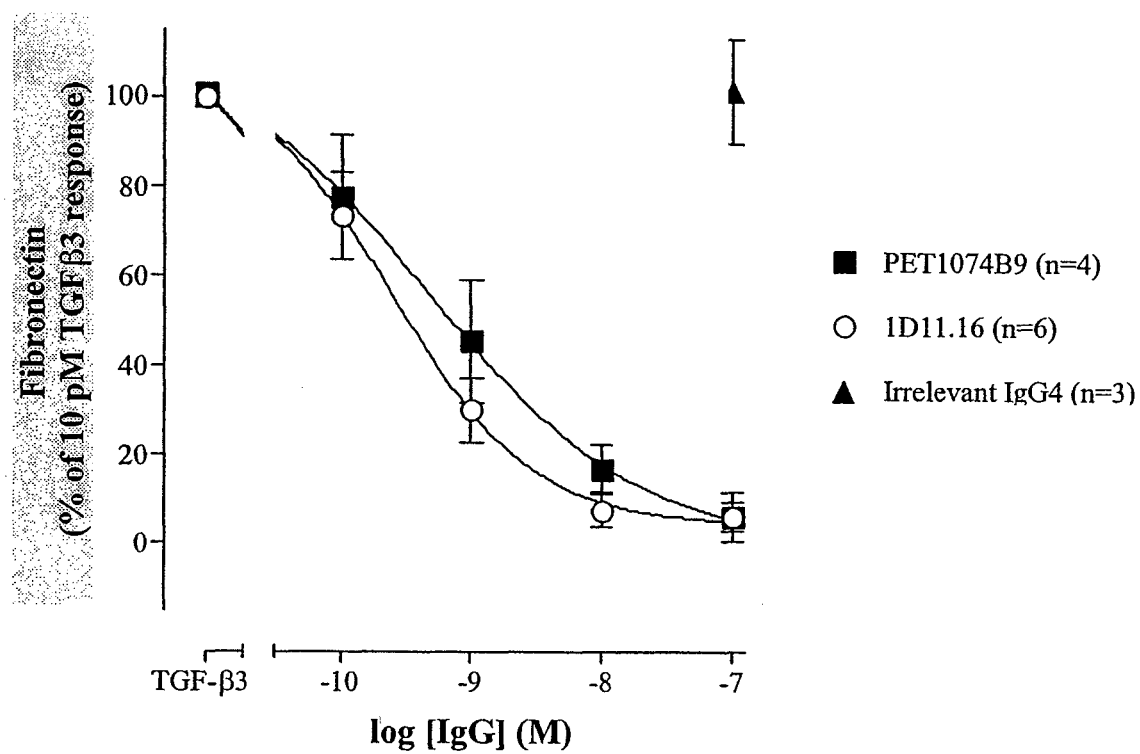
Figure 3A:
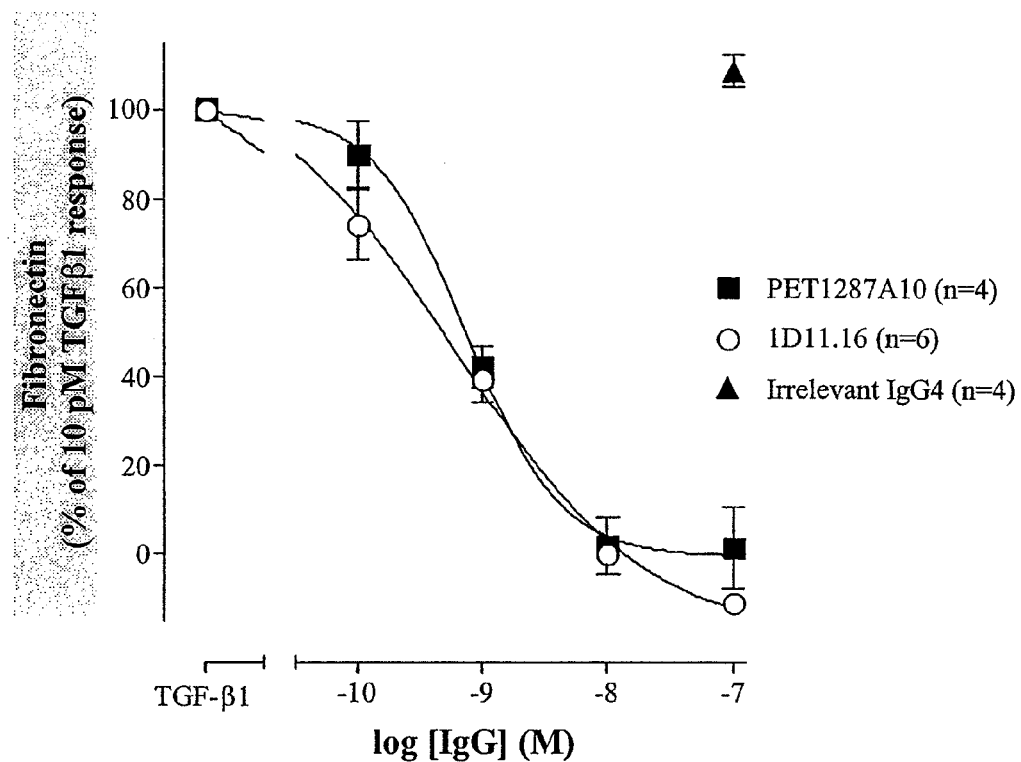
FIG. 3 shows the neutralisation (% inhibition) of TGFβ1 (a), TGFβ2 (b), or TGFβ3 (c) (10 pM)-induced fibronectin production from NHLF cells by PET1287A10 germline IgG4 (closed squares) and 1D11.16 (open circles). The closed triangle represents an irrelevant IgG4 tested at the highest concentration (100 nM). Data are shown as means±SEmean of n experiments performed in duplicate. For $IC_{50}$ values see Table 2.
Figure 3B:
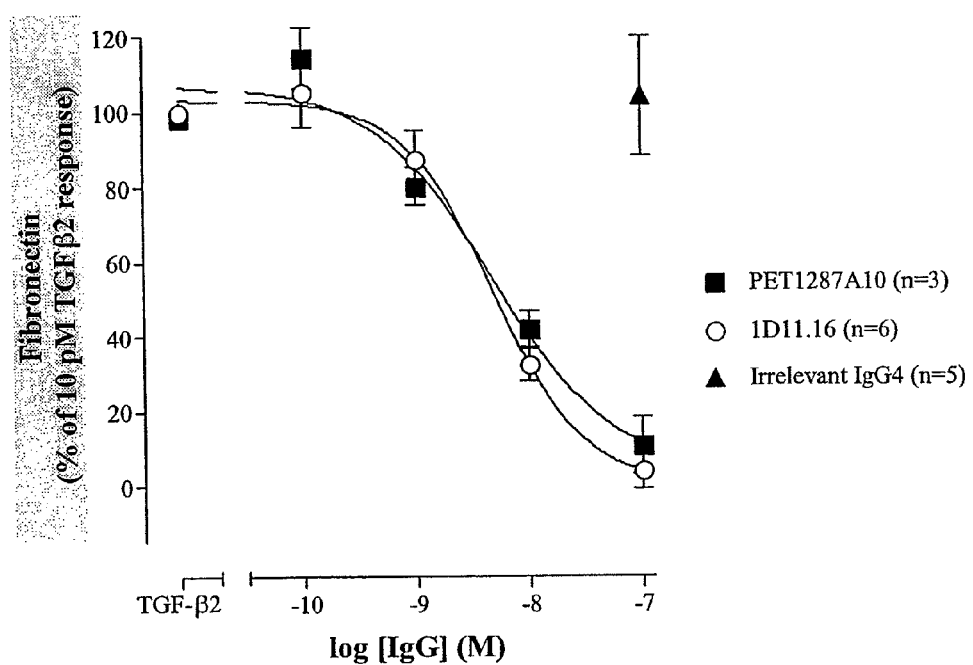
Figure 3C:
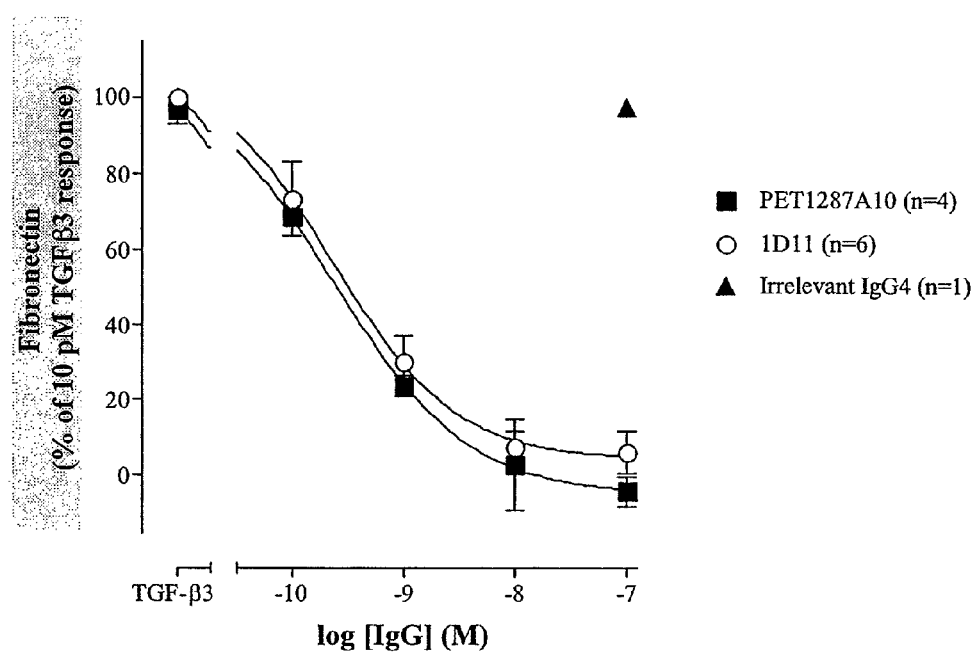

In various aspects of the invention there is provided the subject-matter of the embodiments included below. Further aspects and embodiments of the invention are disclosed in the description herein.

The present invention provides specific binding members for TGFβ, in particular human TGFβ3. Specific binding members that are directed to TGFβ1, TGFβ2 and TGFβ3, are particularly provided. Preferred embodiments within the present invention are antibody molecules, whether whole antibody (e.g. IgG, such as IgG1 or IgG4) or antibody fragments (e.g. scFv, Fab, dAb). Antibody antigen-binding regions and antigen binding sites of antibodies are provided, as are antibody VH and VL domains containing such regions. Within VH and VL domains are provided complementarity determining regions, CDRs, which may be provided within different framework regions, FR's, to form VH or VL domains as the case may be. An antigen binding site may consist of an antibody VH domain and/or a VL domain or antigen-binding portions thereof.

In one aspect, the present invention provides a specific binding member for human TGFβ, comprising an antigen-binding site of an antibody, an HCDR set, an LCDR set, or both and/or a human antibody VH domain, VL domain or both.

The set of HCDR1, HCDR2 and HCDR3 may have sequences selected from the following groups:

HCDR1 SEQ ID NO: 3, HCDR2 SEQ ID NO: 4, HCDR3 SEQ ID NO: 5 (referred to herein as the "PET1073G12 set of HCDRs");

HCDR1 SEQ ID NO: 13, HCDR2 SEQ ID NO: 14, HCDR3 SEQ ID NO: 15 (referred to herein as the "PET1074B9 set of HCDRs");

HCDR1 SEQ ID NO: 23, HCDR2 SEQ ID NO: 24, HCDR3 SEQ ID NO: 25 (referred to herein as the "PET1287A10 set of HCDRs").

The set of LCDR1, LCDR2 and LCDR3 may have sequences selected from the following groups:

LCDR1 SEQ ID NO: 8, LCDR2 SEQ ID NO: 9, LCDR3 SEQ ID NO: 10 (referred to herein as the "PET1073G12 set of LCDRs");

LCDR1 SEQ ID NO: 18, LCDR2 SEQ ID NO: 19, LCDR3 SEQ ID NO: 20 (referred to herein as the "PET1074B9 set of LCDRs");

LCDR1 SEQ ID NO: 28, LCDR2 SEQ ID NO: 29, LCDR3 SEQ ID NO: 30 (referred to herein as the "PET1287A10 set of LCDRs").

The PET1073G12 set of HCDRs together with the PET1073G12 set of LCDRS is herein referred to as the PET1073G12 set of CDRs.

The PET1074B9 set of HCDRs together with the PET1074B9 set of LCDRS is herein referred to as the PET1074B9 set of CDRs.

The PET1287A10 set of HCDRs together with the PET1287A10 set of LCDRS is herein referred to as the PET1287A10 set of CDRs.

A VH domain comprising a set of HCDRs as disclosed herein is also provided by the present invention, as is separately a VL domain comprising a set of LCDRs as disclosed herein. Preferably such a VH domain is paired with such a VL domain, and most preferably the VH and VL domain pairings are the same as in the clones as set out herein.

Further provided by the present invention is a VH domain comprising a set of HCDRs HCDR1, HCDR2 and HCDR3 wherein the set of HCDRs corresponds to that for PET1073G12, PET1074B9 or PET1287A10 with one or two amino acid substitutions.

Further provided by the present invention is a VL domain comprising a set of LCDRs LCDR1, LCDR2 and LCDR3 wherein the set of CDRs corresponds to that for PET1073G12, PET1074B9 or PET1287A10 with one or two amino acid substitutions.

A specific binding member comprising an antigen-binding site of an antibody within such a VH and/or VL domain is also provided by the present invention.

Following the lead of computational chemistry in applying multivariate data analysis techniques to the structure/property-activity relationships (Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)) quantitative activity-property relationships of antibodies can be derived using well-known mathematical techniques such as statistical regression, pattern recognition and classification (Norman et al. Applied Regression Analysis. Wiley-Interscience; 3rd edition (April 1998) ISBN: 0471170828; Abraham Kandel, Eric Backer. Computer-Assisted Reasoning in Cluster Analysis. Prentice Hall PTR; (May 11, 1995), ISBN: 0133418847; Wojtek Krzanowski. Principles of Multivariate Analysis: A User's Perspective (Oxford Statistical Science Series, No 22 (Paper)). Oxford University Press; (December 2000), ISBN: 0198507089; Ian H. Witten, Eibe Frank. Data Mining: Practical Machine Learning Tools and Techniques with Java Implementations. Morgan Kaufmann; (Oct. 11, 1999), ISBN: 1558605525; David G. T. Denison (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369; Arup K. Ghose, Vellarkad N. Viswanadhan. Combinatorial Library Design and Evaluation Principles, Software, Tools, and Applications in Drug Discovery. ISBN: 0-8247-0487-8). The properties of antibodies can be derived from empirical and theoretical models (for example, analysis of likely contact residues or calculated physicochemical property) of antibody sequence, functional and three-dimensional structures and these properties can be considered singly and in combination.

Analysis of antibodies of known atomic structure has elucidated relationships between the sequence and three-dimensional structure of antibody binding sites (Chothia C. et al. Journal Molecular Biology (1992) 227, 799-817; Al-Lazikani, et al. Journal Molecular Biology (1997) 273(4), 927-948). These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions (Chothia et al. and Al-Lazikani et al., supra).

This study of sequence-structure relationship can be used for prediction of those residues in an antibody of known sequence, but of an unknown three-dimensional structure, which are important in maintaining the three-dimensional structure of its CDR loops and hence in maintaining binding specificity. These predictions can be confirmed by comparison of the predictions to the output from lead optimization experiments. In a structural approach, a theoretical model can be created of the antibody molecule (Chothia, et al. Science, 223, 755-758 (1986)) using any freely available or commercial package such as WAM (Whitelegg, N.R.u. and Rees, A. R (2000) Prot. Eng., 12, 815-824). A protein visualisation and analysis software package such as Insight II (Accelerys, Inc.) or Deep View (Guex, N. and Peitsch, M. C. Electrophoresis (1997) 18, 2714-2723) may then be used to evaluate possible substitutions at each position in the CDR and FR. This information may then be used to make substitutions likely to have a minimal or beneficial effect on activity.

The techniques required to make substitutions within amino acid sequences of CDRs, antibody VH or VL domains and specific binding members generally is available in the art. Variant sequences may be made, with substitutions that may or may not be predicted to have a minimal or beneficial effect on activity, and tested for ability to bind and/or neutralise TGFβ and/or for any other desired property. This is discussed further below.

As noted already, the present invention provides specific binding members comprising a defined set of CDRs, in particular the set of CDRs of PET1073G12, PET1074B9 and PET1287A10, and sets of CDRs of PET1073G12, PET1074B9 or PET1287A10 with one or two substitutions within the set of CDRs.

The relevant set of CDRs is provided within antibody framework regions or other protein scaffolds, e.g. fibronectin or cytochrome B. Preferably antibody framework regions are employed.

In a preferred embodiment, the heavy chain utilizes a human $V_H1$ family gene. In various embodiments, the heavy chain framework amino acid sequence contains 1-12, preferably 3-12 and more preferably 3-8 amino acid differences compared to the germline amino acid sequence of the human $V_H1$ family gene. In some embodiments, the heavy chain framework sequence is the germline sequence. In particularly preferred embodiments, the antibody framework region for the heavy chain may be human DP-10 ($V_H$ 1-69) or human DP-88 ($V_H$ 1-e) from the $V_H1$ family. Preferably, embodiments utilizing a human DP-10 gene have a non-germline amino acid at residues 27, 78 and 94. In some embodiments, residue 27 is tyrosine, residue 78 is threonine and residue 94 is serine or leucine. In some embodiments, the light chain utilizes a human Vκ3 family gene with 1-5, preferably 1-4, more preferably 1-3 amino acid differences compared to the germline amino acid sequence. In some embodiments, the light chain framework sequence is the germline human Vκ3 family gene sequence. In particularly preferred embodiments, the framework region for the light chain may be human DPK-22 (A27). In some such embodiments, residue 2 is a non-germline amino acid. In some embodiments residue 2 is a threonine.

In a highly preferred embodiment, a VH domain is provided with the amino acid sequence of SEQ ID NO: 2, this being termed "PET1073G12 VH domain", or SEQ ID NO: 12, this being termed "PET1074B9 VH domain", or SEQ ID NO: 22, this being termed "PET1287A10 VH domain".

In a further highly preferred embodiment, a VL domain is provided with the amino acid sequence of SEQ ID NO: 7, this being termed "PET1073G12 VL domain", or SEQ ID NO: 17, this being termed "PET1074B9 VL domain", or SEQ ID NO: 27, this being termed "PET1287A10 VL domain". A highly preferred embodiment provided in accordance with the present invention is composed of the PET1073G12 VH domain, SEQ ID NO: 2, and the PET1073G12 VL domain, SEQ ID NO: 7. Another highly preferred embodiment provided in accordance with the present invention is composed of the PET1074B9 VH domain, SEQ ID NO: 12, and the PET1074B9 VL domain, SEQ ID NO: 17. Another highly preferred embodiment provided in accordance with the present invention is composed of the PET1287A10 VH domain, SEQ ID NO: 22, and the PET1287A10 VL domain, SEQ ID NO: 27. These or any other antibody antigen-binding site provided in accordance with the present invention may be provided within any desired antibody molecule format, e.g. scFv, Fab, IgG1, IgG4, dAb etc., as is discussed further elsewhere herein.

In a further highly preferred embodiment, the present invention provides an IgG4 antibody molecule comprising the PET1073G12, PET1074B9 or PET1287A10 VH domain, preferably also comprising the corresponding PET1073G12, PET1074B9 or PET1287A10 VL domain.

Other IgG4 or other antibody molecules comprising the PET1073G12, PET1074B9 or PET1287A10 VH domain, and/or the PET1073G12, PET1074B9 or PET1287A10 VL domain, are provided by the present invention as are other antibody molecules comprising the PET1073G12, PET1074B9 or PET1287A10 set of HCDRs within an antibody VH domain, and/or the PET1073G12, PET1074B9 or PET1287A10 set of LCDRs within an antibody VL domain.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As noted, in certain embodiments of the present invention provides a specific binding member which binds all three isoforms of human TGFβ and which comprises the PET1073G12, PET1074B9 or PET1287A10 VH and/or VL domain or antigen-binding portions of those domains.

In some embodiments, a VH domain is paired with a VL domain to provide an antigen binding site. In a preferred embodiment, the PET1073G12 VH domain (SEQ ID NO: 2) is paired with the PET1073G12 VL domain (SEQ ID NO: 7), so that an antigen binding site is formed comprising both the PET1073G12 VH and VL domains. In a preferred embodiment, the PET1074B9 VH domain (SEQ ID NO: 12) is paired with the PET1074B9 VL domain (SEQ ID NO: 17), so that an antigen binding site is formed comprising both the PET1074B9 VH and VL domains. In a preferred embodiment, the PET1287A10 VH domain (SEQ ID NO: 22) is paired with the PET1287A10 VL domain (SEQ ID NO: 27), so that an antibody antigen binding site is formed comprising both the PET1287A10 VH and VL domains. In other embodiments, the PET1073G12, PET1074B9 or PET1287A10 VH is paired with a VL domain other than the corresponding PET1073G12, PET1074B9 or PET1287A10 VL. Light-chain promiscuity is well established in the art.

Similarly, any set of HCDRs disclosed herein can be provided in a VH domain that is used as a specific binding member alone or in combination with a VL domain. A VH domain may be provided with a set of HCDRs as disclosed herein, and if such a VH domain is paired with a VL domain, then the VL domain may be provided with a set of LCDRs disclosed herein. A pairing of a set of HCDRs and a set of LCDRs may be as disclosed herein for the PET1073G12, PET1074B9 and PET1287A10 antibodies. The framework regions of the VH and/or VL domains may be germline frameworks. Frameworks regions of the heavy chain domain may be selected from the $V_H$-1 family, and a preferred $V_H$-1 framework is DP-10 or DP-88 framework. Framework regions of the light chain may be selected from the Vκ3 family, and a preferred such framework is DPK-22.

One or more CDRs may be taken from a VH or VL domain of which the sequence is disclosed herein and incorporated into a suitable framework. This is discussed further herein. The same applies for other CDRs and sets of CDRs of antibodies as obtained using methods described herein.

An antibody VH domain, an antibody VL domain, a set of HCDRs, a set of LCDRs, a set of CDRs, one or more HCDRs e.g. an HCDR3, and/or one or more LCR's e.g. an LCDR3, may be employed in any aspect and embodiment of the present invention as disclosed herein for other molecules, for instance methods of mutation and selection of antigen binding sites with improved potency.

Variants of the VH and VL domains and CDRs of the present invention, including those for which amino acid sequences are set out herein, and which can be employed in specific binding members for TGFβ can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, 4, 3, 2 or 1. Alterations may be made in one or more framework regions and/or one or more CDRs.

In accordance with further aspects of the present invention there is provided a human, humanized, chimeric or synthetic specific binding member that competes or cross-competes for binding to antigen with any specific binding member that both binds the antigen and comprises a specific antibody antigen-binding region, VH and/or VL domain disclosed herein, set of CDRs or HCDR3 disclosed herein, or a variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope. Cross-competition between binding members may be readily assayed by running the reverse assay, e.g., by reversing the tagged and the untagged binding members to identify pairs that block binding in both directions.

Thus, a further aspect of the present invention provides a specific binding member comprising an antigen-binding site of an antibody which competes or cross-competes with a PET1073G12, PET1074B9 or PET1287A10 antibody molecule, in particular PET1073G12, PET1074B9 or PET1287A10 scFv and/or IgG4, for binding to TGFβ. In various embodiments, the antibody is a human, humanized, chimeric or synthetic antibody. In further aspects, the present invention provides a specific binding member comprising an antigen-binding site of a human, humanized, chimeric or synthetic antibody which competes or cross-competes with an antigen-binding site of the present invention for binding to TGFβ, wherein the antigen-binding site of the human, humanized, chimeric or synthetic antibody is composed of a VH domain and a VL domain, and wherein the VH and VL domains comprise a set of CDRs as disclosed herein.

Given the information disclosed herein, various methods are available in the art for obtaining human, humanized, chimeric or synthetic antibodies against TGF and which may compete or cross-compete with a PET1073G12, PET1074B9 or PET1287A10 antibody molecule, an antibody molecule with a PET1073G12, PET1074B9 or PET1287A10 set of CDRs, an antibody molecule with a set of PET1073G12, PET1074B9 or PET1287A10 HCDRs, or an antibody molecule with a set of PET1073G12, PET1074B9 or PET1287A10 LCDRs, for binding to TGFβ.

In a further aspect, the present invention provides a method of obtaining one or more specific binding members able to bind TGFβ1, TGFβ2 and TGFβ3, the method including bringing into contact a library of specific binding members according to the invention and said TGFβs, and selecting one or more specific binding members of the library able to bind all of said TGFβs.

The library may be displayed on the surface of bacteriophage particles, each particle containing nucleic acid encoding the antibody VH variable domain displayed on its surface, and optionally also a displayed VL domain if present.

Following selection of specific binding members able to bind the antigen and displayed on bacteriophage particles, nucleic acid may be taken from a bacteriophage particle displaying a said selected specific binding member. Such nucleic acid may be used in subsequent production of a specific binding member or an antibody VH variable domain (and optionally an antibody VL variable domain) by expression from a nucleic acid with the sequence of nucleic acid taken from a bacteriophage particle displaying a said selected specific binding member.

An antibody VH domain with the amino acid sequence of an antibody VH domain of a said selected specific binding member may be provided in isolated form, as may a specific binding member comprising such a VH domain. Ability to bind all three isoforms of TGFβ may be further tested, also ability to compete or cross-compete with PET1073G12, PET1074B9 or PET1287A10 (e.g. in scFv format and/or IgG format, e.g. IgG4) for binding to all three human isoforms of TGFβ. Ability to neutralise TGF may be tested, as discussed further below.

A specific binding member according to the present invention may bind TGFβ1, TGFβ2 and/or TGFβ3 with the affinity of a PET1073G12, PET1074B9 or PET1287A10 antibody molecule, e.g. scFv, or preferably IgG4, or with an affinity that is greater than one of the above molecules. A specific binding member according to the present invention may neutralise TGFβ1, TGFβ2 and/or TGFβ3 with the potency of a PET1073G12, PET1074B9 or PET1287A10 antibody molecule, e.g. scFv, or preferably PET1073G12, PET1074B9 or PET1287A10 IgG4, or with a potency that is greater than one of the above molecules.

A specific binding member according to the present invention may neutralise naturally occurring TGFβ with the potency of a PET1073G12, PET1074B9 or PET1287A10 antibody molecule, e.g. scFv, or preferably IgG4, or with a potency that is greater than one of the above molecules. Binding affinity and neutralisation potency of different specific binding members can be compared under appropriate conditions.

A preferred embodiment of the present invention comprises preferably human, humanized, chimeric or synthetic antibodies that neutralise naturally occurring TGF with a potency that is equal to or greater than the potency of a TGFβ antigen binding site formed by PET1073G12, PET1074B9 or PET1287A10 VH domain and the corresponding PET1073G12, PET1074B9 or PET1287A10 VL domain.

In addition to antibody sequences, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or a targeting moiety or enzyme (e.g. via a peptidyl bond or linker).

In further aspects, the invention provides an isolated nucleic acid which comprises a sequence encoding a specific binding member, VH domain and/or VL domain or CDR according to the present invention, and methods of preparing a specific binding member, a VH domain and/or a VL domain or CDR of the invention, which methods comprise expressing said nucleic acid under conditions to bring about production of said specific binding member, VH domain and/or VL domain, or CDR and recovering it.

Specific binding members according to the invention may be used in a method of treatment or diagnosis of the human or animal body, such as a method of treatment (which may include prophylactic treatment) of a disease or disorder in a human patient, which comprises administering to said patient an effective amount of a specific binding member of the invention. Conditions treatable in accordance with the present invention include any in which TGF plays a role, especially treatment of fibrotic disease, the modulation of wound healing and the treatment of cancer.

More particularly, specific binding members of the invention are useful to inhibit the activity of any or all of the three isoforms of human TGFβ in vitro or in vivo. Such activities include but are not limited to TGF mediated signaling, extracellular matrix (ECM) deposition, inhibiting epithelial and endothelial cell proliferation, promoting smooth muscle proliferation, inducing Type III collagen expression, inducing TGF-β, fibronectin, VEGF and IL-11 expression, binding Latency Associated Peptide, tumor induced immunosuppression, promotion of angiogenesis, activating myofibroblasts, promotion of metastasis and inhibition of NK cell activity.

Specific binding members of the invention also are useful to treat diseases and conditions that result directly or indirectly from TGFβ activity. Because the specific binding members of the invention are pan-specific, i.e., they bind and inhibit the activity of all three isoforms of TGFβ, they are particularly advantageous for treating conditions and diseases that involve two or more TGFβ isoforms (such as infections and tumors) and severe conditions where inhibiting multiple targets is desirable.

Specific binding members are useful to treat diseases and conditions including, but not limited to, fibrotic diseases (such as glomerulonephritis, neural scarring, dermal scarring, pulmonary fibrosis, lung fibrosis, radiation induced fibrosis, hepatic fibrosis, myelofibrosis), burns, immune mediated diseases, inflammatory diseases (including rheumatoid arthritis), transplant rejection, cancer, Dupuytren's contracture, and gastric ulcers. They are also useful for treating, preventing and reducing the risk of occurrence of renal insufficiencies including but not limited to: diabetic (type I and type II) nephropathy, radiational nephropathy, obstructive nephropathy, diffuse systemic sclerosis, pulmonary fibrosis, allograft rejection, hereditary renal disease (e.g., polycystic kidney disease, medullary sponge kidney, horseshoe kidney), glomerulonephritis, nephrosclerosis, nephrocalcinosis, systemic lupus erythematosus, Sjogren's syndrome, Berger's disease, systemic or glomerular hypertension, tubulointerstitial nephropathy, renal tubular acidosis, renal tuberculosis, and renal infarction. In particular, they are useful when combined with antagonists of the renin-angiotensin-aldosterone system including but not limited to: renin inhibitors, angiotensin-converting enzyme (ACE) inhibitors, Ang II receptor antagonists (also known as "Ang II receptor blockers"), and aldosterone antagonists. Methods for using the specific binding members of the present invention in combination with such antagonists are set forth in PCT/US04/13677, the contents of which are incorporated by reference.

Specific binding members of the invention also are useful to treat diseases and conditions associated with the deposition of ECM, said diseases and conditions including, systemic sclerosis, postoperative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, post angioplasty restenosis, scarring after subarachnoid haemorrhage, multiple sclerosis, fibrosis after laminectomy, fibrosis after tendon and other repairs, scarring due to tattoo removal, biliary cirrhosis (including sclerosing cholangitis), pericarditis, pleurisy, tracheotomy, penetrating CNS injury, eosinophilic myalgia syndrome, vascular restenosis, veno-occlusive disease, pancreatitis and psoriatic arthropathy.

Specific binding members of the invention further are useful in conditions where promotion of re-epithelialization is beneficial. Such conditions include but are not limited to diseases of the skin, such as venous ulcers, ischaemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, oesophageal ulcers (reflex disease), stomach ulcers, small intestinal and large intestinal lesions (inflammatory bowel disease).

Still further uses of specific binding members of the invention are in conditions in which endothelial cell proliferation is desirable, for example, in stabilizing atherosclerotic plaques, promoting healing of vascular anastomoses, or in conditions in which inhibition of smooth muscle cell proliferation is desirable, such as in arterial disease, restenosis and asthma.

Specific binding members of the invention also are useful to enhance the immune response to macrophage-mediated infections such as those caused by *Leishmania* spp., *Trypanosorna cruzi, Mycobacterium tuberculosis* and *Mycobacterium leprae*, as well as the protozoan *Toxoplasma gondii*, the fungi *Histoplasma capsulatum, Candida albicans, Candida parapsilosis*, and *Cryptococcus neoformans*, and *Rickettsia*, for example, *R. prowazekii, R. coronii*, and *R. tsutsugamushi*. They are also useful to reduce immunosuppression caused, for example, by tumors, AIDS or granulomatous diseases.

Specific binding members of the invention further are useful in the treatment of hyperproliferative diseases, such as cancers including but not limited to breast, prostate, ovarian, stomach, renal, pancreatic, colerectal, skin, lung, cervical and bladder cancers, glioma, mesothelioma, as well as various leukemias and sarcomas, such as Kaposi's Sarcoma, and in particular are useful to treat or prevent recurrences or metastases of such tumors. In particular, antagonist specific binding members of the invention are useful to inhibit cyclosporin-mediated metastases.

It will of course be appreciated that in the context of cancer therapy, "treatment" includes any medical intervention resulting in the slowing of tumour growth or reduction in tumour metastases, as well as partial remission of the cancer in order to prolong life expectancy of a patient.

A further aspect of the present invention provides nucleic acid, generally isolated, encoding an antibody VH variable domain and/or VL variable domain disclosed herein.

Another aspect of the present invention provides nucleic acid, generally isolated, encoding a HCDR or LCDR sequence disclosed herein, especially a HCDR selected from SEQ ID NO:'S: 3, 4, 5, 13, 14, 15, 23, 24 and 25 or a VL CDR selected from SEQ ID NO:'S: 8, 9, 10, 18, 19, 20, 28, 29, 30, most preferably PET1073G12, PET1074B9 or PET1287A10 HCDR3 (SEQ ID NO: 5, 15 or 25, respectively). Nucleic acids encoding the PET1073G12, PET1074B9 or PET1287A10 set of CDRs, nucleic acids encoding the PET1073G12, PET1074B9 or PET1287A10 set of HCDRs and nucleic acids encoding the PET1073G12, PET1074B9 or PET1287A10 set of LCDRs are also provided by the present invention, as are nucleic acids encoding individual CDRs, HCDRs, LCDRs and sets of the PET1073G12, PET1074B9 or PET1287A10 CDRs, HCDRs, LCDRs.

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain or causing said antibody VH domain to be expressed in vivo.

Analogous methods for production of VL variable domains and specific binding members comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Particular Embodiments

1. An isolated specific binding member which binds to and neutralizes human TGFβ1, TGFβ2 and TGFβ3, comprising an antigen-binding domain of an antibody, wherein said antigen binding domain comprises a set of CDRs HCDR1, HCDR2 and HCDR3, and wherein said antigen binding domain utilizes a human VH1 family gene and wherein said HCDR3 has an amino acid sequence selected from the group consisting of SEQ ID NO: 5, SEQ ID NO: 15 and SEQ ID NO: 25.
2. The specific binding member according to paragraph 1, wherein the human VH1 family gene is a human VH1-2 gene.
3. The specific binding member according to paragraph 2, where in the human VH1-2 gene is a DP-10 or a DP-88 gene.
4. The specific binding member according to any one of paragraphs 1 to 3, wherein the antigen binding domain further comprises a set of CDRs LCDR1, LCDR2 and LCDR3, and wherein said antigen binding domain utilizes a human Vκ3 family gene and wherein said LCDR3 has an amino acid sequence selected from the group consisting of SEQ ID NO: 10, SEQ ID NO: 20 and SEQ ID NO: 30.
5. The specific binding member according to paragraph 4 wherein the HCDR3 and LCDR3 are selected from the group consisting of:
   (a) SEQ ID NO: 5 and SEQ ID NO: 10, respectively;
   (b) SEQ ID NO: 15 and SEQ ID NO: 20, respectively; and
   (c) SEQ ID NO: 25 and SEQ ID NO: 30, respectively.
6. The specific binding member according to paragraph 4, wherein the human Vκ3 family gene is a human Vκ DPK22 gene.
7. The specific binding member according to paragraph 1, wherein the HCDR1, HCDR2 and HCDR3 of the VH domain are within a germline heavy chain framework.
8. The specific binding member according to paragraph 1, wherein the HCDR1, HCDR2 and HCDR3 of the VH domain are within a framework that comprises up to 12 mutations from the germline amino acid sequence.
9. The specific binding member according to paragraph 4, wherein the LCDR1, LCDR2 and LCDR3 of the Vκ domain are within a germline heavy chain framework.
10. The specific binding member according to paragraph 4, wherein the LCDR1, LCDR2 and LCDR3 of the Vκ domain are within a framework that comprises up to 5 mutations from the germline Vκ amino acid sequence.
11. An isolated specific binding member that binds to and neutralizes human TGFβ1, TGFβ2 and TGFβ3, comprising an antigen-binding domain of an antibody, wherein said antigen binding domain utilizes a human VH DP-10 gene or a human VH DP-88 gene and comprises an FR4 amino acid sequence comprising the amino acid sequence in SEQ ID NO: 31.
12. The specific binding member according to paragraph 11, wherein said antigen binding domain utilizes a human VH DP-10 gene or a human VH DP-88 gene, and comprises a set of CDRs HCDR1, HCDR2 and HCDR3, wherein said HCDR3 has an amino acid sequence selected from the group consisting of SEQ ID NO: 5, SEQ ID NO: 15 and SEQ ID NO: 25, and further comprises an FR4 amino acid sequence comprising the amino acid sequence in SEQ ID NO: 31.
13. The specific binding member according to paragraph 11, wherein the antigen binding domain further utilizes a human Vκ3 family gene and a human Jκ5 gene.
14. The specific binding member according to paragraph 13, wherein said antigen binding domain utilizing a human Vκ3 family gene and a human Jκ5 gene comprises a set of CDRs LCDR1, LCDR2 and LCDR3, and wherein said LCDR3 has an amino acid sequence selected from the group consisting of SEQ ID NO: 10, SEQ ID NO: 20 and SEQ ID NO: 30.
15. An isolated specific binding member which binds to and neutralises human TGFβ1, TGFβ2 and TGFβ3, comprising an antigen-binding domain of an antibody, wherein said antigen binding domain comprises:
   (a) the HCDR1 of amino acid sequence of SEQ ID NO: 3, HCDR2 of amino acid sequence of SEQ ID NO: 4, HCDR3 of amino acid sequence of SEQ ID NO: 5;
   (b) the HCDR1 of amino acid sequence of SEQ ID NO: 13, HCDR2 of amino acid sequence of SEQ ID NO: 14, HCDR3 of amino acid sequence of SEQ ID NO: 15; or
   (c) the HCDR1 of amino acid sequence of SEQ ID NO: 23, HCDR2 of amino acid sequence of SEQ ID NO: 24, HCDR3 of amino acid sequence of SEQ ID NO: 25.
16. The isolated specific binding member according to paragraph 15, wherein the antigen-binding domain further comprises an antibody VL domain.
17. The isolated specific binding member according to paragraph 15, wherein the antigen-binding domain comprises LCDRs are selected from the group consisting of:
   (a) the LCDR1 of amino acid sequence of SEQ ID NO: 8, LCDR2 of amino acid sequence of SEQ ID NO: 9, LCDR3 of amino acid sequence of SEQ ID NO: 10;
   (b) the LCDR1 of amino acid sequence of SEQ ID NO: 18, LCDR2 of amino acid sequence of SEQ ID NO: 19, LCDR3 of amino acid sequence of SEQ ID NO: 20; and
   (c) the LCDR1 of amino acid sequence of SEQ ID NO: 28, LCDR2 of amino acid sequence of SEQ ID NO: 29, LCDR3 of amino acid sequence of SEQ ID NO: 30.
18. The isolated specific binding member according to paragraph 15 wherein HCDR1, HCDR2 and HCDR3 of the VH domain are within a germline heavy chain framework.
19. The isolated specific binding member according to paragraph 18, wherein the germline heavy chain framework is a human VH1 family framework.
20. The isolated specific binding member according to paragraph 15, wherein the HCDR1, HCDR2 and HCDR3 of the VH domain are within germline human heavy chain framework VH1 DP-10 or DP-88.
21. The isolated specific binding member according to paragraph 17, wherein the LCDR1, LCDR2 and LCDR3 of the VL domain are within a germline light chain framework.
22. The isolated specific binding member according to paragraph 21, wherein the germline light chain framework is a human Vκ3 family framework.

23. The isolated specific binding member according to paragraph 21, wherein the antigen binding domain further utilizes a human Jκ5 gene.
24. The isolated specific binding member according to paragraph 22, wherein the human Vκ3 family gene is a Vκ DPK22 gene.
25. An isolated specific binding member comprising the PET10730G12 VH domain (SEQ ID NO: 2) with up to 5 mutations, or an antigen-binding portion thereof.
26. An isolated specific binding member comprising the PET1074B9 VH domain (SEQ ID NO: 12) with up to 5 mutations, or an antigen-binding portion thereof.
27. An isolated specific binding member comprising the PET1287A10 VH domain (SEQ ID NO: 22) with up to 5 mutations, or an antigen-binding portion thereof.
28. The isolated specific binding member according to paragraph 10, further comprising the PET1073G12 VL domain (SEQ ID NO: 7) with up to 5 mutations, or an antigen-binding portion thereof.
29. The isolated specific binding member according to paragraph 25 further comprising the PET1074B9 VL domain (SEQ ID NO: 17) with up to 5 mutations, or an antigen-binding portion thereof.
30. The isolated specific binding member according to paragraph 26 further comprising the PET1287A10 VL domain (SEQ ID NO: 27) with up to 5 mutations, or an antigen-binding portion thereof.
31. An antibody comprising the PET 1073G12 VH domain (SEQ ID NO: 2) and the PET 1073G12 VL domain (SEQ ID NO: 7).
32. An antibody comprising the PET 1074B9 VH domain (SEQ ID NO: 12) and the PET 1074B9 VL domain (SEQ ID NO: 17).
33. An antibody comprising the PET 1287A10 VH domain (SEQ ID NO: 22) and the PET 1287A10 VL domain (SEQ ID NO: 27).
34. The isolated specific binding member according to any one of paragraphs 1 to 33 that comprises an scFv antibody molecule.
35. The isolated specific binding member according to any one of paragraphs 1 to 33 that comprises an antibody constant region.
36. The isolated specific binding member according to paragraph 35 wherein the constant region is from an IgG4.
37. A composition comprising a specific binding member according to any one of paragraphs 1-30 or 34-36.
38. An isolated nucleic acid which comprises a nucleotide sequence encoding a specific binding member according to any one of paragraphs 1-30 or 34-36.
39. A host cell transformed with the nucleic acid according to paragraph 38.
40. A method of producing a specific binding member comprising culturing a host cell according to paragraph 39 under conditions for production of said specific binding member and isolating and/or purifying said specific binding member.
41. The method according to paragraph 40 further comprising formulating the specific binding member or antibody VH or VL variable domain into a composition including at least one additional active component.
42. A method of producing a specific binding member that specifically binds human TGFβ1, TGFβ2 and TGFβ3, which method comprises:
    (a) providing starting nucleic acid encoding a VH domain or a starting repertoire of nucleic acids each encoding a VH domain, wherein the VH domain or VH domains comprise germ-line human framework VH1 DP-10 or DP-88 and either comprise a HCDR1, HCDR2 and/or HCDR3 to be replaced or lack a HCDR1, HCDR2 and/or HCDR3 encoding region;
    (b) combining said starting nucleic acid or starting repertoire with donor nucleic acid or donor nucleic acids, wherein the donor nucleic acid encodes a potential HCDR or the donor nucleic acids encode potential HCDRs, such that said donor nucleic acid is or donor nucleic acids are inserted into the HCDR1, HCDR2 and/or HCDR3 region in the starting nucleic acid or starting repertoire, so as to provide a product repertoire of nucleic acids encoding VH domains;
    (c) expressing the nucleic acids of said product repertoire to produce product VH domains;
    (d) optionally combining said product VH domains with one or more VL domains;
    (e) selecting a specific binding member for human TGFβ1, TGFβ2 and TGFβ3, which specific binding member comprises a product VH domain and optionally a VL domain; and
    (f) recovering said specific binding member or nucleic acid encoding it.
43. The method according to paragraph 42, wherein the donor nucleic acid or donor nucleic acids encode or are produced by mutation of the amino acid sequence of:
    (a) HCDR1 of SEQ ID NO: 3, SEQ ID NO: 13 or SEQ ID NO: 23;
    (b) HCDR2 of SEQ ID NO: 4, SEQ ID NO: 14 or SEQ ID NO: 24; and/or
    (c) HCDR3 of SEQ ID NO: 5, SEQ ID NO: 15 or SEQ ID NO: 25.
44. The method according to paragraph 42 or 43, further comprising fusing the recovered specific binding member to an antibody constant region.
45. The method according to paragraph 42, wherein the specific binding member is an scFv antibody molecule.
46. The method according to paragraph 42, wherein the specific binding member is an Fab antibody molecule.
47. The method according to paragraph 42 wherein the specific binding member is a whole antibody.
48. A method of treating a disease or disorder selected from the group consisting of a fibrotic disease, cancer, or an immune-mediated disease by administering a pharmaceutically effective amount of a composition according to paragraph 37.
49. Use of a specific binding member according to any one of paragraphs 1-30 or 34-36 in the manufacture of a medicament for treatment of a disease or disorder selected from the group consisting of fibrotic disease, cancer, or an immune-mediated disease.
50. A method of inhibiting TGFβ1, TGFβ2 or TGFβ3 signalling comprising the step of contacting TGFβ1, TGFβ32 and TGFβ3 in vivo with a specific binding member according to any one of paragraphs 1-30 or 34-36.
51. A method for inhibiting TGFβ1, 2 or 3-mediated fibronectin production comprising the step of contacting TGFβ1, TGFβ2 and TGFβ3 with a specific binding member according to any one of paragraphs 1-30 or 34-36.
52. A method for inhibiting TGFβ1, 2 or 3-mediated VEGF production comprising the step of contacting TGFβ1, TGFβ2 and TGFβ3 with a specific binding member according to any one of paragraphs 1-30 or 34-36.
53. A method for modulating cell proliferation selected from the group consisting of:
    (a) reducing TGFβ1, 2 or 3-mediated inhibition of epithelial cell proliferation;

(b) reducing TGFβ1, 2 or 3-mediated inhibition of endothelial cell proliferation; and
(c) inhibiting TGFβ1, 2 or 3-mediated smooth muscle cell proliferation, comprising the step of contacting cells expressing TGFβ1, TGFβ2 or TGFβ3 with a specific binding member according to any one of paragraphs 1-29 or 33-35.
54. A method for inhibiting cyclosporin-induced TGFβ1, 2 or 3 activity comprising the step of contacting TGFβ1, TGFβ2 or TGFβ3 with a specific binding member according to any one of paragraphs 1-30 or 34-36.
55. A method for increasing NK cell activity comprising the step of contacting cells expressing TGFβ1, TGFβ2 or TGFβ3 with a specific binding member according to any one of paragraphs 1-30 or 34-36.
56. A method for inhibiting TGFβ1, 2 or 3-mediated immunosuppression comprising the step of contacting cells expressing TGFβ1, TGFβ2 or TGFβ3 with a specific binding member according to any one of paragraphs 1-30 or 34-36.
57. A method for inhibiting the growth of a TGFβ1, 2 or 3 expressing tumor comprising the step of contacting cells expressing TGFβ1, TGFβ2 or TGFβ3 with a specific binding member according to any one of paragraphs 1-30 or 34-36.
58. An isolated specific binding member which specifically binds to and neutralizes TGFβ1, TGFβ32 and TGFβ3 comprising a germline heavy chain framework sequence from the human VH1 gene family.
59. The isolated specific binding member according to paragraph 58, wherein the germline heavy chain framework sequence is from the human DP-10 VH1 gene family.
60. The isolated specific binding member according to paragraph 59, wherein the germline heavy chain framework sequence is from the human DP-88 VH1 gene family.
61. An isolated specific binding member which specifically binds to and neutralizes TGFβ1, TGFβ2 and TGFβ3 comprising a germline light chain sequence from the human Vκ3 gene family.
62. The isolated specific binding member according to paragraph 61, wherein the framework region for the light chain is from DPK-22.
63. The isolated specific binding member according to paragraph 35 wherein the constant region is from an IgG1.

DETAILED DESCRIPTION

Terminology
Specific Binding Member
This describes a member of a pair of molecules which have binding specificity for one another. The members of a specific binding pair may be naturally derived or wholly or partially synthetically produced. One member of the pair of molecules has an area on its surface, or a cavity, which specifically binds to an area on the surface of, or a cavity in, the other member of the pair of molecules. Thus the members of the pair have the property of binding specifically to each other. The present invention is concerned with specific binding members that bind a target antigen.
Specific
This may be used to refer to the situation in which a specific binding member will not show any significant binding to molecules other than its specific binding partner(s) from a given animal. For example, a specific binding member specific for human TGFβ will not have significant binding to other non-TGF-β human molecules however it may cross-react with TGF-β from other species.

An antigen-binding specific binding member comprises an antigen-binding site. For example, a specific binding member may be an antibody molecule. An antigen binding site may also be provided by means of arrangement of CDRs on non-antibody protein scaffolds such as fibronectin or cytochrome B, etc. Koide et al., (1998) Journal of Molecular Biology, 284:1141-1151; Nygren et al. (1997) Current Opinion in Structural Biology, Vol. 7:463-469). Scaffolds for engineering novel binding sites in proteins have been reviewed in detail by Nygren et al., supra. Protein scaffolds for antibody mimics are disclosed in WO 00/34784 which describes proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein.

An advantage of a non-antibody protein scaffold is that it may provide an antigen-binding site in a conserved framework region that is smaller and/or easier to manufacture than at least some antibody molecules. Small size of a specific binding member may confer useful physiological properties such as an ability to enter cells, penetrate deep into tissues or reach targets within other structures, or to bind within protein cavities of the target antigen.

Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site having specificity for binding the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or a targeting moiety or enzyme (e.g. via a peptidyl bond or linker). For example, a specific binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by scaffolds such as fibronectin or cytochrome B (Haan & Maggos, 2004 BioCentury, 12(5): A1-A6; Koide et al., supra; Nygren et al., supra), the structure for carrying a CDR or a set of CDRs of the invention will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., *Sequences of Proteins of Immunological Interest*, 4th Edition, U.S. Department of Health and Human Services, 1987, and updates thereof, now available on the Internet (find "Kabat" using any search engine).

Antibody Molecule

This describes an immunoglobulin whether natural or partly or wholly synthetically produced. The term also covers any polypeptide or protein comprising an antigen binding domain of an antibody. Antibody fragments which comprise an antigen binding domain are molecules such as Fab, scFv, Fv, dAb, Fd and diabodies.

In the genome of a human germline cell, the genetic information for antibody polypeptide chains is contained in multiple gene segments within loci scattered along different chromosomes. Human heavy chains (VH) are encoded on chromosome 14, kappa light chains (Vκ) on chromosome 2 and lambda light chains (Vλ) on chromosome 22. During the development of B-lymphocytes (antibody producing cells), gene segments in these loci are assembled by recombination leading to the formation of complete antibody heavy or light chain genes (Tonegawa S, Nature, 302, 575-81, 1983). Antibody constant regions (VH, Vκ and Vλ) are largely identical throughout the human population but considerable diversity exists within the variable domains. Such diversity enables the development of many billions of different antibodies each with specificity for a different target antigen.

Diversity within the variable regions of antibodies is generated in several ways. Firstly, at the genetic level there is considerable diversity within antibody variable germline gene sequences. Approximately 50 different VH germlines (Tomlinson I. M. et al., J. Mol. Biol., 227, 776-798, 1992), 35 different Vκ germlines (Tomlinson I. M. et al., EMBO J, 14, 4628-38, 1995) and 30 different Vλ germlines (Williams S. C. & Winter G., Eur. J. Immunol, 23, 1456-61, 1993; Kawasaki K. et al., Genome Res, 7, 250-61, 1997) have been described. Antibodies are generated from different combinations of these germline gene sequences. Further diversity is then introduced into antibody variable domains by processes such as somatic recombination and hypermutation (Tonegawa S, Nature, 302, 575-81, 1983).

Although there is considerable diversity within antibody variable germline gene sequences, it is possible to group the sequences into families based on sequence homology. The 50 different VH gene sequences can be grouped into 7 families, the 35 Vκ sequences into 6 families and the 30 Vλ families into 10 families. The groups vary in size from one member (VH6 and Vκ4) to up to 21 members (VH3) and the members of each group share a high degree of sequence homology.

Antibodies can be aligned to VH and VL germline sequence databases to determine their closest germline match and to identify any amino acid changes introduced by somatic hypermutation. Research has shown that the human immune system utilises some germlines (e.g. VH3 DP47) in preference to others (e.g. VH2) during an immune response (Knappik A. et al., J. Mol. Biol, 296, 57-86, 2000). However, populations of antibodies isolated by phage display typically utilise a broad range of germline genes, even when isolated against a single antigen (Edwards B. et al., J. Mol. Biol, 334, 103-118, 2003).

It is possible to take monoclonal and other antibodies and use techniques of recombinant DNA technology to produce other antibodies or chimeric molecules which retain the specificity of the original antibody. Such techniques may involve joining DNA encoding an immunoglobulin variable region to a constant region, or introducing the complementarity determining regions (CDRs), of an antibody into the constant region plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any specific binding member or substance having an antigen-binding site of an antibody with the required specificity. Thus, this term covers antibody fragments and derivatives, including any polypeptide comprising an antigen binding domain, whether natural or wholly or partially synthetic. Chimeric molecules comprising an antigen binding domain of an antibody, or equivalent, fused to another polypeptide are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann et al. (Kontermann R and Dubel Stefan; Antibody Engineering, Springer-Verlag New York, LLC; 2001, ISBN: 3540413545). Phage display, another established technique for generating specific binding members has been described in detail in many publications such as Kontermann et al., supra, and WO 92/01047 (discussed further below). Transgenic mice in which the mouse antibody genes are inactivated and functionally replaced with human antibody genes while leaving intact other components of the mouse immune system, can be used for isolating human antibodies to human antigens (Mendez et al., 1997). Human antibodies, either monoclonal or polyclonal, can also be made in other transgenic animals such as goats, cows, sheep, rabbits, etc.

Synthetic antibody molecules may be created by expression from genes generated by means of oligonucleotides synthesized and assembled within suitable expression vectors, for example as described by Knappik et al., supra or Krebs et al., Journal of Immunological Methods 254 2001 67-84.

It has been shown that fragments of a whole antibody can perform the function of binding antigens. Examples of binding fragments are (i) the Fab fragment consisting of VL, CL, VH and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989), McCafferty et al. (1990) Nature, 348, 552-554) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science, 242, 423-426, 1988; Huston et al., Proc. Natl. Acad. Sci. USA 85, 5879-5883; 1998 viii) bispecific single chain Fv dimers (PCT/US92/09665) and (ix) "diabodies", multivalent or multispecific fragments constructed by gene fusion (WO/13804); F. Holliger et al., Proc. Natl. Acad. Sci. USA 90 6444-6448, 1993). Fv, scFv or diabody molecules may be stabilised by the incorporation of disulphide bridges linking the VH and VL domains (Y. Reiter et al., Nature Biotech, 14, 1239-1245, 1996). Minibodies comprising a scFv joined to a CH3 domain may also be made (S. Hu et al., Cancer Res., 56, 3055-3061, 1996).

A dAb (domain antibody) is a small monomeric antigen-binding fragment of an antibody, namely the variable region of an antibody heavy or light chain (Holt et al., 2003). VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A specific binding member of the present invention may be a dAb comprising a VH or VL domain substantially as set out herein, or a VH or VL domain comprising a set of CDRs substantially as set out herein.

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against TGFβ, then a library can be made where the other arm is varied and an antibody of appropriate specificity selected. Bispecific whole antibodies may be made by knobs-into-holes engineering (C. E. B. Ridgeway et al., *Protein Eng.,* 9, 616-621, 1996).

Antigen-Binding Site

This describes the part of a specific binding member, such as an antibody molecule, that contacts and is complementary to part or all of the other member in the binding pair, i.e., the antigen. In an antibody molecule, the antigen-binding site may be referred to as the antibody antigen-binding site, and comprises the part of the antibody that specifically binds to and is complementary to all or part of the target antigen. Where an antigen is large, an antibody may only bind to a particular part of the antigen, which part is termed an epitope.

Antigen-Binding Domain

An antigen binding domain is a portion of a specific binding member that comprises an antigen-binding site and that binds the target antigen. In some embodiments, an antigen-binding domain may be provided by one or more antibody variable domains (e.g. a so-called Fd antibody fragment consisting of a VH domain) or antigen-binding portions thereof. In some embodiments, an antigen binding domain comprises an antibody light chain variable region (VL) and an antibody heavy chain variable region (VH).

Specific binding members may be glycosylated, either naturally or by systems of various eukaryotic cells (e.g. CHO or NSO (ECACC 85110503) cells), or they may be (for example if produced by expression in a prokaryotic cell) unglycosylated. Glycosylation may also be intentionally altered, for example by inhibiting fucosylation, in order to increase ADCC activity of the resulting antibody. Accordingly, any of the specific binding members of the invention may be expressed so as to minimize or eliminate fucosylation.

In some embodiments, the CDR or VH or VL domain of the invention will be either identical or highly similar to the specified regions of which the sequence is set out herein. It is contemplated that from 1 to 5, preferably from 1 to 4 or 1 or 2, or 3 or 4, amino acid substitutions may be made in the CDR and/or VH or VL domains. VH or VL domains and CDRs and sets of CDRs that are highly similar to those for which sequences are given herein are encompassed by aspects of the present invention, as are those with sequences that are substantially as set out herein.

The structure for carrying a CDR or a set of CDRs of the invention will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, E. A. et al., *Sequences of Proteins of Immunological Interest,* 4th Edition, US Department of Health and Human Services, 1987, and updates thereof, now available on the Internet (find "Kabat" using any search engine). CDRs are defined according to Kabat et al.

CDRs can also be carried by other scaffolds such as fibronectin or cytochrome B.

Preferably, a CDR amino acid sequence substantially as set out herein is carried as a CDR in a human variable domain or a substantial portion thereof. The HCDR3 sequences substantially as set out herein represent preferred embodiments of the present invention and it is preferred that each of these is carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A CDR sequence of the invention (e.g. CDR3) may be introduced into a repertoire of variable domains lacking a CDR (e.g. CDR3), using recombinant DNA technology. Preferred germline frameworks have been identified already herein.

For example, Marks et al. (*Bio/Technology*, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of Vκ variable domains lacking a CDR2. Marks et al. further describe how this repertoire may be combined with a CDR2 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 or any of a subsequent large body of literature, including Kay, B. K., Winter, J., and McCafferty, J. (1996) *Phage Display of Peptides and Proteins: A Laboratory Manual*, San Diego: Academic Press, so that suitable specific binding members may be selected. A repertoire may consist of from $10^4$ individual members upwards, for example from $10^6$ to $10^8$ or $10^{10}$ members. Other suitable host systems include yeast display, bacterial display, T7 display, ribosome display, covalent display and so on.

Analogous shuffling or combinatorial techniques are also disclosed by Stemmer (*Nature,* 1994, 370:389-391), who describes the technique in relation to a β-lactamase gene but observes that the approach may be used for the generation of antibodies.

A further alternative is to generate novel VH or VL regions carrying CDR-derived sequences of the invention using random mutagenesis of one or more selected VH and/or VL genes to generate mutations within the entire variable domain. Such a technique is described by Gram et al. (1992, *Proc. Natl. Acad. Sci., USA,* 89:3576-3580), who used error-prone PCR. In preferred embodiments one or two amino acid substitutions are made within a set of HCDRs and/or LCDRs.

Another method which may be used is to direct mutagenesis to CDR regions of VH or VL genes. Such techniques are disclosed by Barbas et al., (1994, *Proc. Natl. Acad. Sci., USA,* 91:3809-3813) and Schier et al. (1996, *J. Mol. Biol.* 263:551-567).

All the above described techniques are known as such in the art and in themselves do not form part of the present invention. Given the disclosure provided herein, the skilled person will be able to use such techniques to provide specific binding members of the invention using routine methodology in the art.

A further aspect of the invention provides a method for obtaining an antigen binding site of an antibody specific for TGFβ antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antigen binding domain specific for TGFβ and optionally with one or more preferred properties, preferably ability to neutralise TGFβ activity. Said VL domain may have an amino acid sequence which is substantially as set out herein.

An analogous method may be employed in which one or more sequence variants of a VL domain disclosed herein are combined with one or more VH domains.

In a preferred embodiment, PET1073G12, PET1074139 or PET1287A10 VH domain may be subject to mutation to provide one or more VH domain amino acid sequence variants which may be combined with one or more VL domains.

A further aspect of the invention provides a method of preparing a specific binding member specific for all three isoforms of human TGFβ, which method comprises:

(a) providing a starting repertoire of nucleic acids encoding a VH domain which either include a CDR3 to be replaced or lack a CDR3 encoding region;

(b) combining said repertoire with a donor nucleic acid encoding an amino acid sequence substantially as set out herein for a HCDR3 such that said donor nucleic acid is inserted into the CDR3 region in the repertoire, so as to provide a product repertoire of nucleic acids encoding a VH domain;

(c) expressing the nucleic acids of said product repertoire;

(d) selecting a specific binding member specific for at least one isoform of TGFβ; and (e) recovering said specific binding member or nucleic acid encoding it.

The method may further comprise the steps of carrying out binding assays and neutralization assays with each of the three isoforms of TGFβ to identify specific binding members that bind to and neutralize all three isoforms.

Again, an analogous method may be employed in which a LCDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for a specific binding member or specific binding members specific for all isoforms of human TGFβ3.

The VH domain may have a germline sequence, and in preferred embodiments is DP-10 or DP-88. A VL domain sequence may have a germline sequence, and in preferred embodiments is DPK-22.

In a preferred embodiment, one or more of PET1073G12, PET1074B9 or PET1287A10 HCDR1, HCDR2 and HCDR3, or the PET1073G12, PET1074B9 or PET1287A10 set of HCDRs, may be employed, and/or one or more of PET1073G12, PET1074B9 or PET1287A10 LCDR1, LCDR2 and LCDR3, or the PET1073G12, PET1074B9 or PET1287A10 set of LCDRs.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail elsewhere herein.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single specific binding domains, these domains may be used to screen for complementary domains capable of forming a two-domain specific binding member able to bind the three isoforms of human TGFβ.

This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al., ibid.

Specific binding members of the present invention may further comprise antibody constant regions or parts thereof. For example, a VL domain may be attached at its C-terminal end to antibody light chain constant domains including human $C_\kappa$ or $C_\lambda$ chains, preferably $C_\kappa$ chains. Similarly, a specific binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG4 is preferred. IgG4 is preferred for some applications because it does not bind complement and does not create effector functions. Where effector function is desired, IgG1 is preferred. Effector function may also be increased by manipulating the glycosylation state of the antibody, such as by decreasing the fucose content, by methods which are known in the art. The heavy chain may or may not have a C-terminal lysine residue. Any synthetic or other constant region variant that has these properties and stabilizes variable regions is also preferred for use in embodiments of the present invention.

Also within the invention are heterogeneous preparations of the specific binding members or antigen-binding fragments thereof disclosed herein. For example, such preparations may be mixtures of antibodies with full-length heavy chains and heavy chains lacking the C-terminal lysine, with various degrees of glycosylation, with derivatized amino acids, such as cyclization of an N-terminal glutamic acid to form a pyroglutamic acid residue and/or with deamidated forms of the heavy and or light chain.

Specific binding members of the invention may be labelled with a detectable or functional label. Detectable labels include radiolabels such as $^{131}I$ or $^{99}TC$, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Specific binding members of the present invention are designed to be used in methods of diagnosis or treatment in human or animal subjects, preferably human.

In some embodiments, specific binding members of the invention inhibit TGFβ1, 2 and/or 3 binding to a cell surface TGFβ receptor or receptor complex, including but not limited to a complex comprising receptor serine/threonine kinase type I or type II and proteoglycan beta-glycan (TGFβ type III receptor). Accordingly, the invention comprises a method for inhibiting TGFβ binding to a cell surface TGFβ receptor or receptor complex comprising the step of contacting TGFβ with a specific binding member of the invention and detecting inhibition of binding to the receptor or receptor complex. In various embodiments, inhibition of TGFβ binding to its receptor(s) can be indicated by reduced phosphorylation of TGFβ receptor type I, reduced activation of TGFβ receptor type I, reduced phosphorylation of and/or activation of R-SMAD proteins, particularly SMAD2 and SMAD3, reduced translocation of said SMAD proteins to the nucleus, reduced SMAD protein binding to DNA and/or modulation of the expression of a gene whose expression in said cell or cell type is known to be mediated by TGFβ signaling. Further assays are set forth in the examples.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Specific binding members of the invention may be administered by injection (for example, subcutaneously, intravenously, intracavity (e.g., after tumor resection), intralesionally, intraperitoneally or intramuscularly), by inhalation, or topically (for example intraocular, intranasal, rectal, into wounds, on skin), or orally. The route of administration can be determined by the physicochemical characteristics of the product, by special considerations for the disease, by dose or dose interval or by the requirement to optimise efficacy or to minimise side-effects.

It is envisaged that anti-TGFβ treatment will not be restricted to administration by healthcare professionals. Therefore, subcutaneous injection, especially using a needle free device may be appropriate.

In accordance with the present invention, compositions provided may be administered to individuals in need thereof. Administration is preferably in a "therapeutically effective amount", this being sufficient to show benefit to a patient. Such benefit may be at least amelioration of at least one symptom of a particular disease or disorder. The actual amount administered, and rate and time-course of administration, will depend on the nature and severity of the disease being treated. Prescription of treatment, e.g. decisions on dosage etc, may be determined based on preclinical and clinical studies the design of which is well within the level of skill in the art.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 100 μg to 1 gm for systemic applications, and 1 μg to 1 mg for topical applications. Typically, the antibody will be a whole antibody, preferably the IgG4 isotype. This is a dose for a single treatment of an adult patient, which may be proportionally adjusted for children and infants, and also adjusted for other antibody formats in proportion to molecular weight and activity. Treatments may be repeated at daily, twice-weekly, weekly, monthly or other intervals, at the discretion of the physician. In preferred embodiments of the present invention, treatment is periodic, and the period between administrations is about two weeks or more, preferably about three weeks or more, more preferably about four weeks or more, or about once a month.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. Such materials could include, for example, any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. The precise nature of the carrier or other material will depend on the route of administration, which may be oral, topical, by inhalation or by injection, e.g., intravenous. In a preferred embodiment, the antibody is administered by intravenous infusion or injection. In another preferred embodiment, the antibody is administered by intramuscular or subcutaneous injection.

Pharmaceutical compositions for oral administration may be in tablet, capsule, powder or liquid form for example, with an inert diluent or an assimilable edible carrier. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. The specific binding member (and other ingredients, if desired) can also be enclosed in a hard or soft shell gelatin capsule, compressed into tablets, or incorporated directly into the subject's diet. For oral therapeutic administration, the active ingredient can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

For intravenous injection, or injection at the site of affliction, the active ingredient will be in the form of a parenterally acceptable aqueous solution which is pyrogen-free and has suitable pK, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated.

Specific binding members of the present invention may be formulated in liquid, semi-solid or solid forms such as liquid solutions (e.g., injectable and infusible solutions), dispersions or suspensions, tablets, pills, powders, liposomes and suppositories. The preferred form depends on the intended mode of administration, therapeutic application, the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilization, spray drying, or drying by supercritical fluid technology, for example.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the specific binding member in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the antibody compositions active compound may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

The present invention provides a method comprising causing or allowing binding of a specific binding member as provided herein to TGFβ. As noted, such binding may take place in vivo, e.g. following administration of a specific binding member, or nucleic acid encoding a specific binding member, to a patient or it may take place in vitro, for example in ELISA, Western blotting, immunocytochemistry, immuno-precipitation, affinity chromatography, or cell based assays, or in ex vivo based therapeutic methods (e.g., methods in which cells or bodily fluids are contacted ex vivo with a specific binding member according to the invention and then administered to a patient).

The amount of binding of specific binding member to TGFβ may be determined. Quantitation may be related to the amount of the antigen in a test sample, which may be of diagnostic interest.

A kit comprising a specific binding member or antibody molecule according to any aspect or embodiment of the present invention is also provided as an aspect of the present invention. In a kit of the invention, the specific binding member or antibody molecule may be labelled to allow its reactivity in a sample to be determined, e.g. as described further below. Components of a kit are generally sterile and in sealed vials or other containers. Kits may be employed in diagnostic analysis or other methods for which antibody molecules are useful. A kit may contain instructions for use of the components in a method, e.g. a method in accordance with the present invention. Ancillary materials to assist in or to enable performing such a method may be included within a kit of the invention.

The reactivities of antibodies in a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. The signals generated by individual antibody-reporter conjugates may be used to derive quantifiable absolute or relative data of the relevant antibody binding in samples (normal and test).

The present invention also provides the use of a specific binding member as above for measuring antigen levels in a competition assay, that is to say a method of measuring the level of antigen in a sample by employing a specific binding member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a specific binding member according to the invention for example in a biosensor system.

The mode of determining binding is not a feature of the present invention and those skilled in the art are able to choose a suitable mode according to their preference and general knowledge.

As noted, in various aspects and embodiments, the present invention extends to a human, humanized, chimeric or synthetic specific binding member which competes for binding to TGFβ (TGFβ1, 2 and/or 3) with any specific binding member defined herein, e.g. PET1037GR, PET1074B9 or PET1287A10 IgG4. Competition or cross-competition between binding members may be assayed easily in vitro, for example by tagging a specific reporter molecule to one binding member which can be detected in the presence of other untagged binding member(s), to enable identification of specific binding members which bind the same epitope or an overlapping epitope.

Competition may be determined for example using ELISA in which TGFβ is immobilised to a plate and a first tagged binding member (the reference binding member) along with one or more other untagged binding members is added to the plate. Presence of an untagged binding member that competes with the tagged binding member is observed by a decrease in the signal emitted by the tagged binding member.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence. Specific binding members according to the present invention may be such that their binding for antigen is inhibited by a peptide with or including the sequence given. In testing for this, a peptide with either sequence plus one or more amino acids may be used.

Specific binding members which bind a specific peptide may be isolated for example from a phage display library by panning with the peptide(s).

The present invention further provides an isolated nucleic acid encoding a specific binding member of the present invention. Nucleic acid may include DNA and/or RNA. In a preferred aspect, the present invention provides a nucleic acid which codes for a CDR or set of CDRs or antibody antigen-binding site or VH domain or VL domain or antibody molecule, e.g. scFv or IgG4, of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR or set of CDRs or VH domain or VL domain or antigen-binding site or antibody molecule, e.g. scFv or IgG4 as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses an RNA molecule with the specified sequence in which U is substituted for T, unless context requires otherwise.

Systems for cloning and expression of a polypeptide in a variety of different host cells are well known. Suitable host cells include bacteria, mammalian cells, plant cells, insect cells, fungi, yeast and transgenic plants and animals. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others. A common, preferred bacterial host is *E. coli*.

The expression of antibodies and antibody fragments in prokaryotic cells such as *E. coli* is well established in the art. For a review, see for example Plückthun, A. *Bio/Technology* 9: 545-551 (1991). Expression in eukaryotic cells in culture is also available to those skilled in the art as an option for production of a specific binding member for example Chadd HE and Chamow SM (2001) 110 *Current Opinion in Biotechnology* 12: 188-194, Andersen D C and Krummen L (2002) *Current Opinion in Biotechnology* 13: 117, Larrick J W and Thomas D W (2001) *Current Opinion in Biotechnology* 12:411-418.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, or adenoviral, AAV, lentiviral, etc. as appropriate. For further details see, for example, *Molecular Cloning: A Laboratory Manual,* 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1986, *Short Protocols in Molecular Biology: A Compendium of Methods from Current Protocols in Molecular Biology*, Ausubel et al. eds., John Wiley & Sons, 4th edition 1999. The disclosures of Sambrook et al. and Ausubel et al. (both) are incorporated herein by reference.

Thus, a further aspect of the present invention provides a host cell containing nucleic acid as disclosed herein. Such a host cell may be in vitro and may be in culture. Such a host cell may be in vivo. In vivo presence of the host cell may allow intracellular expression of the specific binding members of the present invention as "intrabodies" or intracellular antibodies. Intrabodies may be used for gene therapy (Marasco W A (1997) *Gene Therapy*, 4(1): 11).

A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may incorporated into the host cell or into an artificial chromosome (Csonka E et al. (2000) *Journal of Cell Science*, 113: 3207-3216; Vanderbyl S et al. (2002) *Molecular Therapy*, 5(5: 10. Incorporation may be either by random or targeted integration of one or mere copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

The nucleic acid molecules of the instant invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein. Methods of utilizing an anti-TGFβ antibody in gene therapy are known in the art. See, for example, U.S. Pat. No. 5,824,655 (Border), which is incorporated herein by reference in its entirety.

In a preferred embodiment, the gene therapy method comprises the steps of administering an isolated nucleic acid molecule encoding the heavy chain or an antigen-binding portion thereof of an anti-TGFβ antibody and expressing the nucleic acid molecule. In another embodiment, the gene therapy method comprises the steps of administering an isolated nucleic acid molecule encoding the light chain or an antigen-binding portion thereof of an anti-TGFβ antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-TGFβ antibody of the invention and expressing the nucleic acid molecules.

Dose-correction across species generally requires an adjustment for body-weight only, if the active agent is an antibody acting in or close to the vascular system. Effective doses of the antibodies of the invention have been 0.5-5 mg/kg in rat and mouse in the acute setting. Therefore, for long-term dosing, 0.3-10 mg/kg administered on the half-life (expected to be in the region of 21 days in humans) is considered likely. Preferable doses are sufficient for efficacy, but low enough to facilitate optimal administration. For example a dose of less than 50 mg facilitates subcutaneous administration. Intravenous administration is preferable in early clinical trials and may be used as the route of delivery for severe diseases if the dose is high and the dosing interval long. Subcutaneous injection is generally more convenient than intravenous delivery, because it allows self-administration. However, subcutaneous injection has the potential to augment any immune response to product. Local administration for localized disease can minimize the amount of product required and maximize the concentration at the site of action. A significant safety (therapeutic window) advantage may be conferred by local administration, avoiding any potential side effects that may develop from chronic systemic administration.

Further aspects and embodiments of the present invention will be apparent to those skilled in the art in the light of the present disclosure, including the following experimental exemplification. All documents referred to anywhere in this specification are incorporated by reference.

EXAMPLE 1

Generation of Anti-TGFβ ScFvs
ScFv Naive Antibody Libraries
  A large single chain Fv (scFv) human antibody library derived from spleen lymphocytes from 20 donors and cloned into a phagemid vector (Hutchings et al., 2001) was used for selections.
ScFv Guided Selection Libraries
  A 1D11.16 VH-human VL library was constructed and used to select mouse-human chimeric antibodies with the desired binding properties. The human light chains from these chimeric antibodies were then cloned into human VH-VL and human VH (1D11 CDR3)-VL acceptor libraries. These libraries were screened for human antibodies with the desired binding properties.
Selection of ScFv Phage Libraries
  Recombinant human TGFβ1 and TGFβ2 were supplied by Genzyme Corp. (Framingham, Mass.) and TGFβ3 was purchased from R&D Systems.
  ScFvs which recognised TGFβ were isolated from scFv guided selection libraries following a series of repeated selection cycles on recombinant human TGF essentially as described in Vaughan et al. (1996). In brief, following incubation with the library, the immobilised antigen, which had been pre-coupled to paramagnetic beads, and bound phage were recovered by magnetic separation whilst unbound phage were washed away. Bound phage was then rescued as described by Vaughan et al. (1996) and the selection process repeated.

Selections were performed using TGFβ1, TGFβ2 or TGFβ3 coupled to Dynabeads M-270 amine (Dynal) according to the manufacturer's recommendations. Alternatively, selections used biotinylated TGFβ1 or TGFβ2 prepared using the primary amine specific reagent succinimidyl-6-(biotinannido) hexanoate following the manufacturer's instructions (EZ link NHS LC Biotin, Pierce).

Outputs from selections were tested as periplasmic preparations in high throughput screens based on competition assays which measured the ability of the scFvs present in the periplasmic preparation to compete with 1D11.16 or the recombinant human TGFβ soluble receptor II-Fc chimaera (sRII, R&D Systems) for binding to TGFβ.

Samples that competed with 1D11.16 or sRII in the high throughput screens were subjected to DNA sequencing as described in Vaughan et al. (1996) and Osbourn et al. (1996). Clones were expressed and purified as scFvs or IgGs and assessed for their ability to neutralise TGFβs in the MLEC and/or the NHLF assays as described in Examples 4 and 5 respectively. Purified scFv preparations were prepared as described in Example 3 of WO 01/66754. Protein concentrations of purified scFv preparations were determined using the BCA method (Pierce). Purified IgG preparations were prepared as described below in Example 3.

EXAMPLE 2

Optimisation of Anti-TGFβ scFvs

ScFvs binding and neutralising TGFβ were generated as described in Example 1. The neutralisation potencies of these antibodies were increased on TGFβ1 and/or TGFβ2 and/or TGFβ3 using DNA mutagenesis and/or combinatorial techniques. Antibodies with significantly improved potencies on TGFβ1 and/or TGFβ2 and/or TGFβ3 were generated by selecting and screening phage antibody libraries essentially as described in Example 1. The scFvs generated were compared to 1D11.16 in the MLEC proliferation assay.

Particular germlines were found to be highly represented amongst the population of high potency, TGFβ-neutralising scFvs. These were DP-10/1-69 and DP-88/1-e (both members of the VH1 germline family) for the heavy chain, and DPK22/A27 ($V_\kappa 3$ family) for the light chain. These germlines appear to provide a structural framework particularly suitable for high potency, TGFβ pan-neutralising antibodies. This was not predictable, since 1D11.16 VH gene segment is closest to the human germline DP-7 and the 1D11.16 VL gene segment is closest to the human germline L16.

PET1073G12, PET1074B9 and PET1287A10 scFvs showed potencies approaching or exceeding those of 1D11.16 on all three TGFβ isoforms in the MLEC proliferation assay.

The derived amino acid sequences of PET1073G12, PET1074B9 and PET1287A10 VH and VL gene segments were aligned to the known human germline sequences in the VBASE database (Tomlinson et al., 1997) and the closest human germline identified by sequence similarity. The closest human germline gene for the VH gene segment of PET1073G12 and PET1074B9 was identified as DP-10/1-69 (VH1 germline family) and the closest human germline gene for the VH gene segment of PET1287A10 was identified as DP-88/1-e (VH1 germline family). The closest human germline gene for the VL gene segment of PET1073G12, PET1074B9 and PET1287A10 was identified as DPK22/A27 ($V_\kappa 3$ germline family). Site directed mutagenesis was used to change framework residues that differed from germline to the germline residue, provided that such changes did not produce a loss of potency in the MLEC proliferation assay of more than three-fold in the resulting antibody on any TGFB. isoform. If such a loss of potency was observed, the non-germline framework amino acid was kept in the final antibody.

In germlined PET1073G12 and germlined PET1074B9 all framework residues are germline except for two residues in VH and one residue in VL. The amino acid sequences for germlined PET1073G12 are described in SEQ ID NO: 2 for VH and SEQ ID NO: 7 for VL. The amino acid sequences for germlined PET1074B9 are described in SEQ ID NO: 12 for VH and SEQ ID NO: 17 for VL.

In germlined PET1287A10 all VH and VL framework residues are germline. The amino acid sequences for germlined PET1287A10 are described in SEQ ID NO: 22 for VH and SEQ ID NO: 27 for VL.

EXAMPLE 3

Production of IgG4s

The germlined scFvs PET1073G12, PET1074B9 and PET1287A10 were converted from the scFv format to the IgG4 format by sub-cloning their VH and VL domains into vectors expressing whole antibody heavy and light chains respectively. The VH gene segment was amplified from the pCantab6 scFv expressing vector and cloned into the pEU8.1 (+) vector containing the human γ4 heavy chain constant domains and regulatory elements to express the whole heavy chain in mammalian cells. Similarly, the VL gene segment was amplified from the pCantab6 scFv-expressing vector and cloned into the pEU3.1(−) vector containing the human K light chain constant domains and regulatory elements to express the whole light chain in mammalian cells. The pEU3.1(−) and pEU8.1 (+) vectors were based on the vectors described by Persic et al., (1987) and were modified to introduce the oriP sequence to increase the yields of antibody produced (Shen. et al., 1995; Langle-Rouault et al., 1998). Following cloning, the VH and VL domains of all three antibodies were sequenced to confirm that no mutations had been introduced during the cloning procedure.

Vectors for the expression of PET1073G12, PET1074B9 and PET1287A10 heavy and light chain were transfected into EBNA-293 cells (Invitrogen). Following gene expression and secretion in the cell supernatant, PET1073G12, PET1074B9 and PET1287A10 IgG4s were purified by protein A affinity chromatography (Amersham). The purified antibody preparations were sterile filtered and stored at 4° C. in phosphate buffered saline (PBS) prior to evaluation. The concentration of IgG was determined spectrophotometrically using an extinction coefficient based on the amino acid sequence of the IgG as described in Mach et al. (1992). The purified IgG were analysed by SEC-HPLC using a Biosep-SEC-S2000 column (Phenomenex) to check for aggregation or degradation of the protein. Reformatted human IgG4 whole antibodies were compared to the 1D11.16 antibody in the MLEC and NHLF cell based assays as described in Examples 4 and 5 respectively.

EXAMPLE 4

Neutralisation Potency of Anti-TGFβ Antibodies in the TGFβ Dependent MLEC Proliferation Assay The neutralisation potency of purified antibody preparations against human TGFβ bioactivity was assessed using the Mink Lung Epithelial Cell (MLEC) proliferation assay.

The MLEC proliferation assay is based on an assay described by Danielpour et al. (1989a). This assay works on the principle that when TGFβ1, TGFβ2 or TGFβ3 is added to mink lung epithelial cells this causes an inhibition of the serum induced cell proliferation. Antibodies were tested for neutralisation of TGFβ1, TGFβ2 or TGFβ3 resulting in the restoration of the cell proliferation. Proliferation was measured by the uptake of [$^3$H]-thymidine. The potency of the antibody was defined as the concentration of the antibody that neutralised a single concentration of TGFβ1, TGFβ2 or TGFβ3 at a level of 50% ($IC_{50}$) in nM.

MLEC Proliferation Assay Protocol

Plating of MLEC

The MLEC line was obtained from the American Type Culture Collection (Cat.# CCL-64). Cells were grown in Minimum Essential Media (MEM, Gibco) containing 10% FBS (Gibco), 1% penicillin/streptomycin (Gibco) and 1% MEM non essential amino acids solution (Gibco). Confluent cells from T-175 flasks were dissociated from the flask, spun down, washed, and resuspended in MLEC assay media that was made of MEM containing 1% FBS, 1% penicillin/streptomycin and 1% MEM non essential amino acids solution. An aliquot of the cells was then labelled with trypan blue, counted on a haemocytometer and the cell stock diluted to $1.75 \times 10^5$ cell per ml using assay media. 100 µl of this suspension was added to each well of a tissue culture flat-bottomed 96 well plate and incubated for 3 to 5 hours.

Preparation of TGFβ/Antibody Solutions

Working solutions of TGFβ1, TGFβ2 or TGFβ3 at 6 ng/ml (6 times the final assay concentration) and antibodies (including controls such as 1D11.16) at 3 times the final maximum assay concentration were prepared in MLEC assay media. The final concentration of TGFβ in the assay (1 ng/ml or 40 pM) corresponded to the concentration that induced approximately 80% inhibition of cell proliferation compared to the control with no TGFβ (i.e. $EC_{80}$ value).

Dilution Plate Set Up

Samples of test and control antibodies were titrated in 3-fold dilution steps in MLEC assay media and incubated in the presence and absence of TGFβ1, TGFβ2 or TGFβ3. All relevant controls were included in every experiment: testing of the 1D11.16 and/or reference antibody as appropriate and performing TGFβ1, TGFβ2 or TGFβ3 titrations. Completed plates were left in a humidified tissue culture incubator for 1 hour±15 minutes.

Addition of TGFβ/Antibody Solutions to the Plated Cells

After the appropriate incubation times, 100 µl from each well of the dilution plates were transferred to the plated MLEC and the plates returned to the incubator for 44±2 hours.

Addition of [$^3$H]-Thymidine

25 µl of 10 µCi/ml [$^3$H]-thymidine (diluted in PBS) was added to each of the wells (0.25 µCi/well). The plates were then returned to the incubator for 4 hours±30 minutes.

Cell Harvesting

100 µL of trypsin-EDTA (0.25%, Gibco) was added to each well, plates incubated for 10 minutes in the incubator and cells were harvested using a Tomtec or Packard 96 well cell harvester.

Data Accumulation and Analysis

Data from the harvested cells were read using a beta-plate reader (TopCount, Packard). Data were analysed to obtain $IC_{50}$ and standard deviation values. $IC_{50}$ values were obtained by using the Prism 2.0 (GraphPad) software.

Results

Purified PET1073G12, PET1074B9 and PET1287A10 germlined IgG4s were tested alongside 1D11.16 in the MLEC proliferation assay. IgG4s were produced as described in Example 3. Arithmetic mean $IC_{50}$s±standard deviation (where $IC_{50}$ is the concentration of antibody required to neutralise 40 pM TGFβ1, TGFβ2 or TGFβ3 by 50%) are shown in Table 1.

Mean $IC_{50}$ data for PET1073G12 and PET1287A10 IgG4s shows that these antibodies have potencies similar or approaching those of 1D11.16 on TGFβ1, TGFβ2 and TGFβ3.

Mean $IC_{50}$ data suggests that PET1074B9 IgG4 is significantly more potent on TGFβ1 (although a full dose response curve was not obtained in the MLEC assay). As a means for comparison, 1D11.16 showed 12% neutralisation on TGFβ1 at a concentration of 91 pM and PET1074B9 showed 78% neutralisation at a similar concentration of 92 pM. Furthermore, PET1074B9 was also tested alongside 1D11.16 in a normal human lung fibroblast assay (NHLF) fibronectin production assay (Example 5). The results obtained in the NHLF assay confirm those obtained in the MLEC assay: PET1074B9 has potencies similar to those of 1D11.16 on TGFβ2 and TGFβ3 and PET1074139 is more potent than 1D11.16 on TGFβ1.

EXAMPLE 5

Neutralisation Potency of Anti-TGFβ Antibodies in the TGFβ3 Dependent NHLF Cell Assay The neutralisation potency of purified antibody preparations against human TGFβ bioactivity was assessed using the Normal Human Lung Fibroblast (NHLF) fibronectin production assay. This assay measures the ability of antibodies to neutralise the production of the extracellular matrix (ECM) glycoprotein, fibronectin. TGFβs are potent stimulators of fibronectin production in cultured fibroblasts (Ignotz and Massaoue, 1986) exerting their effects via activation of the c-Jun N-terminal kinase pathway (Hocevar et al., 1999).

NHLF Cell Assay Protocol

NHLF cells were obtained from Clonetics™ and maintained in complete fibroblast growth media-2 (FGM-2) in a humidified atmosphere containing 5% $CO_2$ at 37° C. At 90-100% confluence, fibroblasts were plated ($1.5 \times 10^5$/well, 24 well format) in 1.5 ml FGM-2 media and allowed to attach for 24 hours at 37° C. Cells were washed with serum-free fibroblast basal media (FBM) and serum starved overnight in 1.5 ml FBM supplemented with human insulin (100 µg/ml), gentamicin/fungizone (50 µg/ml) and ascorbic acid (50 µg/ml) and incubated for 24 hours at 37° C. All experiments were performed on cells between passage three to six.

Preparation of TGFβ and Antibody Solutions

Working solutions of TGFβ1, TGFβ2 or TGFβ3 at 25 ng/ml (1 nM) and antibodies (including controls such as 1D11.16) were prepared in assay media. The final concentration of TGFβ in the assay (250 pg/ml or 10 pM) corresponded to the concentration that induced approximately 80% stimulation of fibronectin production compared to control with no TGFβ (i.e. $EC_{80}$ value).

Dilution Plate Set Up

Samples of test and control antibodies were serially diluted in 10-fold dilution steps in assay media and preincubated in the presence and absence of TGFβ1, TGFβ2 or TGFβ3 32 for 30 minutes. NHLF cells were incubated in 2 ml/well assay media for 48 hours at 37° C. After 48 hours a 0.5 ml aliquot of culture media supernatant was taken for fibronectin analysis by ELISA.

Human Fibronectin ELISA

Fresh or frozen (−20° C.) NHLF supernatant samples were analysed using a Technoclone™ human fibronectin antigen ELISA kit comprising of a human anti-fibronectin capture monoclonal antibody (clone 6FN) and a HRP conjugated monoclonal anti-fibronectin secondary antibody. The methodology was as follows:

Nunc-Immuno™ Maxisorp™ 96 well plates were coated (1 μg/well) with an anti-fibronectin capture antibody in coating buffer (12 mM $Na^2CO_3$, 35 mM $NaHCO^3$, 0.01% (w/v) thimerosal in distilled water, pH 9.6) for 16 hours at 4° C. The capture antibody was removed and each well blocked with 100 μl of dilution buffer (1% (w/v) BSA in PBS) for 1 hour at 37° C. After washing three times with wash buffer (250 μg/well of 0.5% (v/v) Tween 20 in PBS), human plasma fibronectin standards and samples were added to the plate and incubated for 1 hour at 37° C. The plate was then washed three times and incubated with an anti-fibronectin HRP secondary antibody (100 μg/well in dilution buffer) for 30 minutes at 37° C. The plate was washed three times with wash buffer and 100 μg/well of tetramethylbenzidine (TMB) substrate was added to the plate. After incubation of the plate at room temperature for 20 minutes, the reaction was stopped with 100 μg/well 2 M sulphuric acid. The absorbance at 450 nm was then measured using a Dynex MRX plate reader.

Data Analysis

Data are presented as a percentage of the control response to the TGFβ isoform under test (100%). Geometric mean pIC50 values and 95% confidence limits were estimated using four-parameter logistic curve fitting (Prism 2, GraphPad Software, San Diego, USA). When a four parameter fit failed, three or two parameter fit was performed by holding the curve top and/or bottom values constant.

Results

Purified PET1073G12, PET1074B9 and PET1287A10 germlined IgG4s were tested alongside 1D11.16 in the NHLF fibronectin production assay. IgG4s were produced as described in Example 3. Arithmetic mean $IC_{50}$s±standard deviation (where $IC_{50}$ is the concentration of antibody required to neutralise 10 pM TGFβ1, TGFβ2 or TGFβ3 by 50%) are shown in Table 2.

EXAMPLE 6

Potency in IL-11 Induction Assay

We assessed the neutralisation potency of purified antibody preparations against human TGFβ bioactivity using a A549 cell (human lung epithelial carcinoma cells) IL-11 induction assay.

We maintained A549 cells (ATCC, Part #: CCL-185) in Growth/Assay Media (435 mL DMEM, 50 mL fetal bovine serum (FBS), 5 mL penicillin/streptomycin, 5 mL Modified Eagle Medium non-essential amino acids, 5 mL 100×L-glutamine; all Gibco/Invitrogen). At approximately 90% confluence, we plated the cells in 100 μL Growth/Assay Media and allowed cells to attach for 24 hours at 37° C., 5% $CO_2$.

Preparation of TGFβ and Antibody Solutions

We prepared working solutions of TGFβ1 (1.8 ng/ml), TGFβ2 (4.2 ng/ml) or TGFβ3 (4.2 ng/ml) and antibodies (including controls) in Growth/Assay media.

Dilution Plate Set Up

We serially diluted samples of test and control antibodies in 5-fold (TGFβ2 or TGFβ3) or 10-fold (TGFβ1) dilution steps in Growth/Assay media and preincubated in the presence and absence of TGFβ1, TGFβ2 or TGFβ3 at 37° C. for 75 minutes. We incubated A549 cells in 200 μl/well assay media for 18-24 hours at 37° C. After 18-24 hours, a 100 μl aliquot of culture media supernatant was taken for IL-11 analysis by ELISA.

EXAMPLE 7

To determine the biologic efficacy of a human pan-neutralizing TGF-β monoclonal antibody for treating chronic renal disease and other clinical indications characterized by pathogenic fibrosis, we studied the effect of the antibody in a rat unilateral ureteral obtruction (UUO) model.

Adult Sprague Dawley rats (Taconic Farms, Germantown, N.Y.) weighing 250-280 gram (about 6 weeks) were housed in an air-, temperature-, and light-controlled environment. Rats undergoing UUO received a small ventral midline abdominal incision to expose the left kidney and upper ureter. We ligated the ureter at the level of the lower pole of the kidney with silk suture and a second time at about 0.2 cm below the first one. Sham operated rats received the same surgical protocol but without ureteral ligation.

The obstructed rats were treated with PBS, a murine pan-neutralizing monoclonal antibody (1D11), an isotype-matched control antibody (13C4) or a human pan-neutralizing TGF-β monoclonal antibody of the invention as follows. We administered the antibodies to the rats intraperitoneally beginning on the day of ureteral ligation for a course of 3 weeks. 13C4 and 1D11 were administered at 5 mg/kg (3 times/week) and the human pan-neutralizing antibody was given to the rats at 5 mg/kg (every 5 days).

At the end of 3 weeks, we sacrificed the rats, perfused the kidneys with PBS for 3 minutes and harvested the perfused kidneys for the analysis of mRNA, determination of collagen content and histological examination.

To assess the extent of tissue fibrosis, we determined total tissue collagen content by biochemical analysis of hydroxyproline in hydrolysate extracts according to Kivirikko et al. This assay is based on the observation that essentially all hydroxyproline in animal tissues is found in collagen.

We also performed a Sircol collagen assay for total collagen content. The Sircol collagen assay measures the amount of total acid/pepsin soluble collagens based on the specific binding of Sirius red dye with the side chain of tissue collagen.

The UUO rats treated with the human pan-neutralizing monoclonal antibody showed a 43.4% reduction in hydroxyproline content (1.98±0.26 μg/mg dry tissue) when compared to the PBS treated group (3.5±0.3 μg/mg dry tissue, p<0.05). The lessening in renal fibrosis was further supported by the reduction in total solubilized collagen in the affected kidneys, as determined by a Sirius red dye based assay (sham: 18.5±2.6, PBS: 69.3±3.8, and human pan-neutralizing monoclonal antibody: 35.6±5.2 μg/100 mg tissue, p<0.05 vs. PBS).

We also assessed the ability of a human pan-neutralizing anti-TGF-β monoclonal antibody to reduce tissue fibrosis by immunohistochemical examination.

In control animals, ureteral obstruction for three weeks caused widespread disruption of renal tubular architecture with marked distension, cellular atrophy and necrosis/apoptosis, tissue inflammation and tubulointerstitial expansion with evident fibrosis. There was little evidence of glomerular damage. Rats treated with 1D11 or the human pan-neutralizing monoclonal antibody, on the other hand, showed preservation of renal architecture as judged by attenuated tubular dilation and disorganization, reduced inflammatory infiltrates (cellularity) and diminished tubulointerstitial expansion and fibrosis.

We also measured the effect of treatment with a human pan-neutralizing anti-TGF-β monoclonal antibody on TGF-β regulated gene expression.

TGF-β1 mRNA was significantly reduced in the human pan-neutralizing monoclonal antibody treated UUO animals compared to either PBS-treated or 13C4 control antibody-treated animals. A significant decrease in mRNA levels for type III collagen also was seen in the obstructed kidneys treated with the human and murine anti-TGF-β antibodies as compared to those treated with PBS or 13C4 indicating a decrease in collagen synthesis.

We further confirmed the efficacy of a human pan-neutralizing anti-TGF-β monoclonal antibody to reduce auto-induced TGF-β synthesis by measuring the total renal TGF-β1 protein.

Compared to the sham-operated animals, obstructed kidneys exhibited a marked increase in total tissue TGF-β1. Obstructed rats dosed with a human pan-neutralizing monoclonal antibody, however, showed 75% reduction of tissue TGF-β1 levels, significantly below the levels recorded for both control groups. By comparison, the murine 1D11 antibody reduced tissue TGF-β1 levels by 45%, compared to control groups.

The above-described results demonstrate that the TGF-β, neutralization with a human pan-neutralizing anti-TGF-β monoclonal antibody effectively interrupted the TGF-β autocrine-regulation loop concomitant with prevention of TGF-β1 production and collagen III mRNA expression.

We further determined the effect of a human pan-neutralizing anti-TGF-β monoclonal antibody on the expression of smooth muscle actin (α-SMA) as an indirect indicator of TGF-β inhibition. Smooth muscle actin expression is an indicator of activated myofibroblasts, which are associated with tissue fibrosis and produce fibrous connective tissue. TGF-β is an important inducer of the activation and phenotypic transformation of stromal fibroblasts and resident epithelial cells to myofibroblastic cells.

We detected α-SMA protein by standard Western blot analysis.

When compared with sham-operated animals, rats with obstructed kidneys showed dramatic upregulation in α-SMA protein as measured by western blotting of tissue homogenates (data not shown). Obstructed rats dosed with a human pan-neutralizing anti-TGF-β monoclonal antibody showed significant reduction (75% compared to PBS controls) in measureable α-SMA expression.

These results demonstrate the efficacy of a human pan-neutralizing anti-TGFβ monoclonal antibody in reducing collagen deposition in the fibrotic kidneys, clearly indicating that the antibody is a potent inhibitor of renal collagen production and deposition in this model of severe renal injury and tubulointerstitial fibrosis. Because the process of tissue fibrosis in organs such as in lung, liver or kidney possesses common mechanisms or pathways, the skilled worker will appreciate that the antibody is useful in the treatment of chronic renal diseases as well as other clinical indications characterized by pathogenic fibrosis.

A description of certain preferred claims of the invention follows:

TABLE 1

| TGFβ isoform | Geometric Mean $IC_{50}$ (95% confidence intervals; nM) | | | |
|---|---|---|---|---|
| | PET1073G12 n = 6 | PET1074B9 n = 6 | PET1287A10 n = 5 | 1D11.16 n = 25 |
| TGFβ1 | 0.8 (0.3-2.2) | <1# | 1.8 (1-3.6) | 3.9 (2.9-5.2) |
| TGFβ2 | 13.0 (8.7-18.7) | 1.5 (1.1-2.2) | 25.0 (13.3-47.0) | 9.2 (7.3-11.5) |
| TGFβ3 | 6.0 (4.2-8.4) | 2.0 (1-4.1) | 0.5 (0.2-1) | 1.0 (0.5-2.0) |

Neutralisation of the anti-proliferative effects of TGFβ1, TGFβ2 and TGFβ3 on MLEC using PET1073G12, PET1074B9 or PET1287A10 germlined IgG4s or 1D11.16. The total number of data points for each mean is indicated by n number, and represents an independent titration of each antibody. # $IC_{50}$ values could not be determined as the antibody was too potent in the concentration range tested and a full dose response curve was not obtained.

TABLE 2

| TGFβ isoform | Geometric Mean $IC_{50}$ (95% confidence intervals) | | | |
|---|---|---|---|---|
| | PET1073G12 n = 5 | PET1074B9 n = 4 | PET1287A10 n = 4 | 1D11.16 n = 6 |
| TGFβ1 | 0.44 (0.24-0.82) | 0.18 (0.14-0.28) | 0.8 (0.44-1.3) | 0.4 (0.19-0.96) |
| TGFβ2 | 12.0 (5.4-26) | 4.6 (1.9-11) | 3.9 (0.9-16.6) | 4.0 (1.9-8.3) |
| TGFβ3 | 2.8 (1.27-6.5) | 0.28 (0.02-3.45) | 0.45 (0.25-0.79) | 0.16 (0.04-0.18) |

Potencies of PET1073G12, PET1074B9 or PET1287A10 germlined IgG4s or 1D11.16 in the NHLF assay. The total number of data points for each mean is indicated by n number, and represents an independent titration of each antibody.

We claim:

1. An isolated nucleic acid encoding the heavy chain, the light chain, or both, of a specific binding member that binds to human TGFβ1, TGFβ2 and TGFβ3, said specific binding member comprising an antigen-binding portion of an antibody
wherein the heavy chain of the antibody comprises an HCDR1 comprising the amino acid sequence of SEQ ID NO: 3, an HCDR2 comprising the amino acid sequence of SEQ ID NO: 4, and an HCDR3 comprising the amino acid sequence of SEQ ID NO: 5; and
wherein the light chain of the antibody comprises an LCDR1 comprising the amino acid sequence of SEQ ID NO: 8, an LCDR2 comprising the amino acid sequence of SEQ ID NO: 9, and an LCDR3 comprising the amino acid sequence of SEQ ID NO: 10.

2. The isolated nucleic acid according to claim 1, wherein the specific binding member is an antibody comprising:
   a) the PET1073G12 $V_H$ domain (SEQ ID NO: 2);
   b) the PET1073G12 $V_L$ domain (SEQ ID NO: 7); or
   c) both a) and b).

3. The isolated nucleic acid according to claim 2, wherein the antibody further comprises a human IgG4 constant region.

4. The isolated nucleic acid according to claim 2, wherein the antibody further comprises a human IgG1 constant region.

5. The isolated nucleic acid according to claim 1, wherein the specific binding member is a single chain Fv molecule comprising:
   a) the PET1073G12 $V_H$ domain (SEQ ID NO: 2);
   b) the PET1073G12 $V_L$ domain (SEQ ID NO: 7); or
   c) both a) and b).

6. The isolated nucleic acid according to claim 1, wherein the specific binding member neutralizes human TGFβ1, TGFβ2 and TGFβ3.

7. The isolated nucleic acid according to claim 1, wherein the heavy chain of the antibody comprises an FR4 amino acid sequence comprising the amino acid sequence of SEQ ID NO: 31.

8. The isolated nucleic acid according to claim 1, wherein the antibody comprises the PET1073G12 $V_H$ domain (SEQ ID NO: 2) with up to 5 framework mutations.

9. The isolated nucleic acid according to claim 1, wherein the antibody comprises the PET1073G12 $V_L$ domain (SEQ ID NO: 7) with up to 5 framework mutations.

10. The isolated nucleic acid according to claim 1, wherein the specific binding member is an antibody, wherein the heavy chain of the antibody comprises the PET1073G12 $V_H$ domain (SEQ ID NO: 2) and a human IgG4 constant region, and wherein the light chain of the antibody comprises the PET1073G12 $V_L$ domain (SEQ ID NO: 7) and a human κ light chain constant region.

11. A host cell transformed with the nucleic acid according to claim 1 or 10.

12. A method of producing a specific binding member, comprising:
culturing a host cell according to claim 11 under conditions for production of said specific binding member, and
isolating and/or purifying said specific binding member,
wherein the host cell comprises a nucleotide sequence encoding the heavy chain, and a nucleotide sequence encoding the light chain, of the antigen-binding portion of the antibody.

13. The method according to claim 12, further comprising formulating the specific binding member into a composition including at least one additional active component.

14. The method according to claim 12, wherein the specific binding member is an scFv antibody molecule.

15. The method according to claim 12, wherein the specific binding member is an Fab antibody molecule.

16. The method according to claim 12, wherein the specific binding member is a whole antibody.

* * * * *